United States Patent
Mangalam et al.

(10) Patent No.: US 12,281,290 B2
(45) Date of Patent: Apr. 22, 2025

(54) SYSTEMS AND METHODS FOR MEASURING MAT DENSITY OF AQUATIC BIOMASS

(71) Applicant: Plantible Foods Inc., San Marcos, CA (US)

(72) Inventors: Geoffrey Mangalam, San Marcos, CA (US); Maurits Van De Ven, San Marcos, CA (US); Fedor Kuzminov, San Marcos, CA (US); Edward Chen, San Marcos, CA (US); Sheldon Compton, San Marcos, CA (US); Matthew McAuliffe, Vista, CA (US)

(73) Assignee: Plantible Foods Inc., San Marcos, CA (US)

( * ) Notice: Subject to any disclaimer, the term of this patent is extended or adjusted under 35 U.S.C. 154(b) by 0 days.

(21) Appl. No.: 18/598,606

(22) Filed: Mar. 7, 2024

(65) Prior Publication Data
US 2024/0263114 A1 Aug. 8, 2024

Related U.S. Application Data

(63) Continuation of application No. PCT/US2022/076040, filed on Sep. 7, 2022.
(Continued)

(51) Int. Cl.
*C12M 1/00* (2006.01)
*G01N 21/53* (2006.01)
(Continued)

(52) U.S. Cl.
CPC ............ *C12M 21/02* (2013.01); *C12M 31/10* (2013.01); *C12M 41/06* (2013.01); *G01N 21/534* (2013.01);
(Continued)

(58) Field of Classification Search
CPC ...... C12M 21/02; C12M 31/10; C12M 41/06; G01N 21/534; G01N 21/59; G01N 21/85; G01N 33/18; G01N 33/487
See application file for complete search history.

(56) References Cited

U.S. PATENT DOCUMENTS

| 4,087,566 A | 5/1978 | Kim |
| 4,338,340 A | 7/1982 | Morimoto |

(Continued)

FOREIGN PATENT DOCUMENTS

| AU | 2018256629 B2 | 10/2020 |
| CN | 104596448 B | 5/2015 |

(Continued)

OTHER PUBLICATIONS

Buyel et al., Flocculation increases the efficacy of depth filtration during the downstream processing of recombinant pharmaceutical proteins produced in tobacco, Plant Biotechnol J, 2014, vol. 12, p. 240-252.
(Continued)

*Primary Examiner* — Tri T Ton
(74) *Attorney, Agent, or Firm* — Greenberg Traurig, LLP

(57) ABSTRACT

Provided are methods, devices, and systems for measuring aquatic biomass in an aqueous liquid, optionally for the cultivation, growth optimization, and harvest of an aquatic biomass for plant protein production. In particular, measurements of aquatic biomass density are based on light absorption of the aquatic biomass. The aquatic biomass includes an aquatic organism such as *Lemna*, including *Lemna minor*. The plant protein isolates include a RuBisCO protein.

47 Claims, 10 Drawing Sheets
Specification includes a Sequence Listing.

Related U.S. Application Data

(60) Provisional application No. 63/241,627, filed on Sep. 8, 2021.

(51) Int. Cl.
    *G01N 21/59*     (2006.01)
    *G01N 21/85*     (2006.01)
    *G01N 33/487*     (2006.01)

(52) U.S. Cl.
    CPC ............ *G01N 21/59* (2013.01); *G01N 21/85* (2013.01); *G01N 33/487* (2013.01)

(56) References Cited

U.S. PATENT DOCUMENTS

| | | |
|---|---|---|
| 6,033,895 A | 3/2000 | Garger |
| 7,337,782 B2 | 3/2008 | Thompson |
| 8,529,976 B2 | 9/2013 | Mcmindes |
| 8,685,707 B2 | 4/2014 | Ploechinger |
| 9,175,052 B2 | 11/2015 | Gerardi |
| 9,301,544 B2 | 4/2016 | Mua |
| 9,655,376 B2 | 5/2017 | Ergun |
| 10,039,306 B2 | 8/2018 | Vrljic |
| 10,172,380 B2 | 1/2019 | Varadan |
| 10,457,906 B2 | 10/2019 | Green |
| 10,745,682 B2 | 8/2020 | Sebastian |
| 10,757,964 B2 | 9/2020 | Ford |
| 10,798,950 B2 | 10/2020 | Walther |
| 10,834,959 B2 | 11/2020 | Ford |
| 2004/0247760 A1 | 12/2004 | Howsam |
| 2006/0288449 A1 | 12/2006 | Garger |
| 2008/0181990 A1 | 7/2008 | Ledbetter |
| 2009/0151240 A1 | 6/2009 | Kayama |
| 2010/0003741 A1 | 1/2010 | Fromson |
| 2010/0136201 A1 | 6/2010 | Bigeard |
| 2012/0011090 A1 | 1/2012 | Tang |
| 2012/0100901 A1 | 4/2012 | Kirsch |
| 2012/0117869 A1 | 5/2012 | Javan |
| 2012/0155714 A1 | 6/2012 | Douglass |
| 2015/0133636 A1 | 5/2015 | Xenopoulos |
| 2015/0335043 A1 | 11/2015 | De Jong |
| 2016/0029663 A1 | 2/2016 | Gerardi |
| 2016/0192697 A1 | 7/2016 | Mua |
| 2017/0105438 A1 | 4/2017 | Ajami |
| 2017/0164651 A1 | 6/2017 | Mua |
| 2018/0020676 A1 | 1/2018 | Taghavi |
| 2018/0362957 A1 | 12/2018 | Sebastian |
| 2019/0021390 A1 | 1/2019 | Ford |
| 2019/0133163 A1 | 5/2019 | Varadan |
| 2019/0259108 A1 | 8/2019 | Timo |
| 2019/0364948 A1 | 12/2019 | Tetrick |
| 2020/0022946 A1 | 1/2020 | Brener |
| 2020/0347376 A1 | 11/2020 | Sebastian |
| 2021/0022387 A1 | 1/2021 | Ford |
| 2021/0177000 A1 | 6/2021 | Schmitt |
| 2021/0259290 A1 | 8/2021 | Ajami |
| 2021/0347818 A1 | 11/2021 | Lihme |

FOREIGN PATENT DOCUMENTS

| | | | |
|---|---|---|---|
| CN | 108487205 B | | 9/2018 |
| CN | 109137864 B | | 1/2019 |
| CN | 110271650 A | | 9/2019 |
| CN | 111199195 A | | 5/2020 |
| CN | 210827402 U | | 6/2020 |
| CN | 111903323 A | | 11/2020 |
| CN | 110271650 B | | 2/2021 |
| CN | 112376514 A | | 2/2021 |
| CN | 212714866 U | | 3/2021 |
| CN | 212772269 U | | 3/2021 |
| CN | 114751484 A | * | 7/2022 |
| EP | 3011836 A1 | | 4/2016 |
| JP | 2015002751 A | | 1/2015 |
| JP | 2018131414 A | | 8/2018 |
| JP | 2019010105 A | | 1/2019 |
| WO | 2008043147 A1 | | 4/2008 |
| WO | 2010144877 A1 | | 12/2010 |
| WO | 2011078671 A1 | | 6/2011 |
| WO | 2013096700 A1 | | 6/2013 |
| WO | 2014004018 A1 | | 1/2014 |
| WO | 2014104880 A1 | | 7/2014 |
| WO | 2014165769 A1 | | 10/2014 |
| WO | 2015153666 A1 | | 10/2015 |
| WO | 2016201379 A1 | | 12/2016 |
| WO | 2018008030 A1 | | 1/2018 |
| WO | 2020143515 A1 | | 7/2020 |
| WO | 2021007484 A1 | | 1/2021 |
| WO | 2021008680 A1 | | 1/2021 |
| WO | 2021034980 A1 | | 2/2021 |
| WO | 2023039419 A2 | | 3/2023 |
| WO | 2024136679 A1 | | 6/2024 |

OTHER PUBLICATIONS

Gregory et al., Adsorption and flocculation by polymers and polymer mixtures, Adv. Colloid Interface Sci, 2011, vol. 169, p. 1-12.

International Search Report and Written Opinion for PCT/US2023/060574, mailed Oct. 25, 2023.

Torkata et al., Protein Coagulation through Reversible and Irreversible Bindings of Calcium, Agricultural and Biological Chemistry, 1987, vol. 5, No. 3, p. 707-714.

International Search Report and Written Opinion for PCT/US2022/076040, mailed Jul. 19, 2023.

Abckroos, Water Lentil Protein Concentrate, BRS Biorefinery Solutions, 1 pg, Oct. 1, 2019.

Anonymous, Plantible Foods, Plant-based nutrition for all Humanity, 2018, p. 1-6.

Balasubramanian et al., "Recycling of biogas-plant effluent through aquatic plant (*Lemna*) culture," Bioresource Technology, 1992, vol. 41, Issue 3, pp. 213-216.

Cole et al., "Population genetic structure in duckweed (*Lemna minor, Lemnaceae*)," Can. J. Bot., 1996, vol. 74, 222-230.

Compeer et al. Interreg Vlaanderen-Nederland, Applications of proteins, amino acids and starch from duckweed, Avans University of Applied Sciences, 2018, p. 1-21.

Cui et al., "Growing duckweed for biofuel production: A review," Plant Biol (Stuttg). 2015, 17 Suppl 1, pp. 16-23.

Deckers, et al., "Structuring Processes for Meat Analogues," Trends Food Sci. Technol., 2018, 81, pp. 25-36.

Douillard et al., Leaf protein for food use: potential of Rubisco, New and Developing Sources of Food Proteins, 1994, p. 307-342.

Edelman et al., Nutrient Value of Leaf vs. Seed, Frontiers in Chemistry, 2016, vol. 4, p. 1-5.

Erb et al., Exploring the biophysical option space for feeding the world without deforestation, Nat. Comms., (2016), vol. 7, p. 1-9.

Ferreira et al., An accurate method to quantify ribulose bisphosphate carboxylase content in plant tissue, Plant, Cell and Environ. 2000, vol. 23, p. 1329-40.

Ferreira et al., Immunological Exercises for Beginners, Biochemical Education, vol. 24, p. 176-178.

Ferreira, Sulfur Starvation in Lemna Leads to Degradation of Ribulose-Bisphosphate Carboxylase without Plant Death, J. Biol. Chem., 1992, vol. 267, p. 7253-57.

Godfray et al., Meat consumption, health, and the environment, Science, 2018, vol. 361, eeam65324, p. 1-10.

Haustein, et al., "Compensatory growth in boiler chicks fed on Lemna gibba," British Journal of Nutrition, 1992, vol. 63, pp. 329-335.

Immonen, et al., "Texturization of a Blend of Pea and Destarched Oat Protein Using High-Moisture Extrusion," Foods, Food Engineering and Technology Section, 2021, vol. 10(1517), p. 1-14.

International Search Report and Written Opinion for PCT/US2020/041525, mailed Dec. 3, 2020.

International Search Report and Written Opinion for PCT/US2022/025737 mailed Oct. 5, 2022.

International Search Report and Written Opinion for PCT/US2022/078017, mailed Aug. 15, 2023.

(56) References Cited

OTHER PUBLICATIONS

Ishizawa et al., "Evaluation of environmental bacterial communities as a factor affecting the growth of duckweed *Lemna minor*," Biotechnology for Biofuels, 2017, vol. 10, Issue 62, pp. 1-10.

Kalburgi, Evaluation of RuBisCO extraction methods using the aquatic plant, *Lemna*, Professional Science Masters in Biotechnology, 2019, p. 1-19.

Kinsella, Functional Properties of Proteins, Possible Relationship Between Structure and Function in Foams, Food Chemistry, 1981, vol. 7, p. 273-288.

Libouga et al., Thermal denaturation and gelation of rubisco: effects of pH and ions, Int. J. Biological Macromolecules, 1996, vol. 19, p. 271-77.

Ma et al., "Large-scale screening and characterisation of Lemna aequinoctialis and Spirodela polyrhiza strains for starch production," Plant Biol (Stuttg), 2018, vol. 20, Issue 2, pp. 357-364.

Machovina et al., Biodiversity conservation: The key is reducing meat consumption, Science of the Total Environment, (2016), vol. 536, p. 419-431.

Mardanov et al., Complete Sequence of the Duckweed (*Lemna minor*) Chloroplast Genome: Structural Organization and Phylogenetic Relationships to Other Angiosperms, Journal of Molecular Evolution, 2022, vol. 66, p555-564.

Martin et al., Characterization of Heat-Set Gels from RuBisCo in Comparison to Those from Other Proteins, J. Agric. Food Chem., 2014, vol. 62, p. 10783-91.

Maung et al., "Asian Perspective on High-Moisture Extrusion," Cereal Foods World, 2020, vol. 65, p. 1-6.

Mestameyer et al., Solar Energy Conversion Efficiency and Growth Aspects of the Duckweed, *Spirodela punctata, Aquatic Botany*, (1984) 19: 157-70.

NCBI, Large subunit of riblose-1,5-bisphosphate carboxylase/oxygenase (chloroplast), Accession No. YP-001595516, retrieved from internet Aug. 24, 2022.

Nieuwland et al., Isolation and Gelling Properties of Duckweed Protein Concentrate, ACS Food Sci Technol, 2021, vol. 1, p. 908-916.

Oron et al., "Effect of wastes quality on treatment efficient with duckweed," Water Sci. Technol., 1989, vol. 21, pp. 639-645.

Osen, et al., "High Moisture Extrusion Cooking of Pea Protein Isolates: Raw Material Characteristics, Extruder Responses, and Texture Properties," J. Food Eng., 2014, 127, pp. 67-74.

Phan-Xuan et al., Hydration-Induced Structural Changes in the Solid State of Protein: A SAXS/WAXS Study on Lysozyme, Mol. Pharmaceutics, 2020, vol. 17, p. 3246-3258.

Rusoff et al., Duckweeds (*Lemnaceae* Family): A Potential Source of Protein and Amino Acids, J. Agric. Food Chem, 1980, vol. 28, p. 848-850.

Steinfeld et al., Livestock's Long Shadow: Environmental Issues and Options, (2006) Food and Agriculture Organization of the United Nations.

Stomp, "The duckweeds: a valuable plant for biomanufacturing," Biotechnol Annu Rev., 2005, vol. 11, pp. 69-99.

Thermo Scientific, Protein stability and storage, Thermo Scientific, 2009, p. 1-3.

Van De Velde II, From waste product to food ingredient: The extraction of abundant plant protein RuBisCo, New Food Magazine, 2011, Issue 2, Article, p. 1-9.

Vermaat et al., "Performance of common duckweed species (*Lemnaceae*) and the waterfern Azolla filiculoides on different types of waste water," Water Research, 1998, vol. 32, Issue 9, pp. 2569-2576.

Vymazal "Constructed Wetlands for Wastewater Treatment," Encyclopedia of Ecology, 2019, vol. 1, pp. 14-21.

Wendeou, et al., "Influence of Salinity on Duckweed Growth and Duckweed Based Wastewater Treatment System," Journal of Water Resource and Protection, 2013, vol. 5, pp. 993-999.

Whitepaper, Water Activity [aw] in Foods, Safefood 360, Inc., 2014, p. 1-9.

Wittek, et al., "High Moisture Extrusion of Soy Protein: Investigations on the Formation of Anisotropic Product Structure," Foods, 2021, vol. 10, p. 1-17.

Yin et al., "The influence of light intensity and photoperiod on duckweed biomass and starch accumulation for bioethanol production," Bioresour Technol., 2015, vol. 187, pp. 84-90.

Yu, et al., "Comparative analysis of duckweed cultivation with sewage water and SH media for production of fuel ethanol," PLoS One, 2014, p. 1-15, e115023.

Zhang, et al., "Converting Peanut Protein Biomass Waste into "Double Green" Meat Substitutes Using a High-Moisture Extrusion Process: A Multiscale Method to Explore a Process for Forming a Meat-Like Fibrous Structure," J. Agric. Food Chem., 2019, vol. 67, p. 10713-10725.

\* cited by examiner

```
                           SEQUENCE LISTING

Sequence total quantity: 10
SEQ ID NO: 1             moltype = AA   length = 478
FEATURE                  Location/Qualifiers
source                   1..478
                         mol_type = protein
                         organism = Lemna minor
SEQUENCE: 1
MSPQTETKAS AGFKAGVKDY KLNYYTPEYE TKDTDILAAF RVTPQPGVPP EEAGAAVAAE   60
SSTGTWTTVW TDGLTSLDRY KGRCYHIEPV AGEENQFIAY IAYPLDLFEE GSVTNMFTSI  120
VGNVFGFKAL RALRLEDLRI PPAYSKTFQG PPHGIQVERD KLNKYGRPLL GCTIKPKLGL  180
SAKNYGRAVY ECLRGGLDFT KDDENVNSQP FMRWRDRFLF CAEAIYKAQA ETGEIKGHYL  240
NATAGTCEEM IKRAVFAREL GVPIVMHDYL TGGFTANTSL AYYCRDNGLL LHIHRAMHAV  300
IDRQKNHGMH FRVLAKALRM SGGDHVHSGT VVGKLEGERE MTLGFVDLLR DDFIEKDRSR  360
GIFFTQDWVS MPGVLPVASG GIHVWHMPAL TEIFGDDSVL QFGGGTLGHP WGNAPGAVAN  420
RVALEACVKA RNEGRDLARE GNEIIREACN WSPELAAACE VWKEIKFEYE PVDKLDVK    478

SEQ ID NO: 2             moltype = AA   length = 177
FEATURE                  Location/Qualifiers
source                   1..177
                         mol_type = protein
                         organism = Lemna minor
SEQUENCE: 2
MASSMMASTA AAVARAGPAQ SSMVPFNACR SSVPFPATRK ANNNLSTLPG NGGRVSCMQV   60
WPPEGLKKFE TLSYLPPLSV EDLAKEVDYL LRNDWVPCIE FSKEGFVYRE NHASPGYYDG  120
RYWTMWKLPM FGCTDASQVI AEVEEAKKAY PEYFVRIIGF DNKRQVQCIS FIAYKPT     177

SEQ ID NO: 3             moltype = AA   length = 477
FEATURE                  Location/Qualifiers
source                   1..477
                         mol_type = protein
                         organism = Nicotiana tabacum
SEQUENCE: 3
MSPQTETKAS VGFKAGVKEY KLTYYTPEYQ TKDTDILAAF RVTPQPGVPP EEAGAAVAAE   60
SSTGTWTTVW TDGLTSLDRY KGRCYRIERV VGEKDQYIAY VAYPLDLFEE GSVTNMFTSI  120
VGNVFGFKAL RALRLEDLRI PPAYVKTFQG PPHGIQVERD KLNKYGRPLL GCTIKPKLGL  180
SAKNYGRAVY ECLRGGLDFT KDDENVNSQP FMRWRDRFLF CAEAIYKAQA ETGEIKGHYL  240
NATAGTCEEM IKRAVFAREL GVPIVMHDYL TGGFTANTSL AHYCRDNGLL LHIHRAMHAV  300
IDRQKNHGIH FRVLAKALRM SGGDHIHSGT VVGKLEGERD ITLGFVDLLR DDFVEQDRSR  360
GIYFTQDWVS LPGVLPVASG GIHVWHMPAL TEIFGDDSVL QFGGGTLGHP WGNAPGAVAN  420
RVALEACVKA RNEGRDLAQE GNEIIREACK WSPELAAACE VWKEIVFNFA AVDVLDK     477

SEQ ID NO: 4             moltype = AA   length = 181
FEATURE                  Location/Qualifiers
source                   1..181
                         mol_type = protein
                         organism = Nicotiana tabacum
SEQUENCE: 4
MAFLIMSSAA AVATGTNAAQ ASMIAPFTGL KSATSFPVSR KQNLDITSIA SNGGRVQCMQ   60
VWPPINKKKY ETLSYLPDLS EEQLLREVEY LLKNGWVPCL EFETEHGFVY RENNKSPGYY  120
DGRYWTMWKL PMFGCTDATQ VLAEVEEAKK AYPQAWIRII GFDNVRQVQC ISFIAYKPEG  180
Y                                                                  181

SEQ ID NO: 5             moltype = AA   length = 474
FEATURE                  Location/Qualifiers
source                   1..474
                         mol_type = protein
                         organism = Medicago sativa
SEQUENCE: 5
MSPQTETKAT VGFKAGVKDY RLTYYTPDYE TKDTDILAAF RVSPQPGVPA EEAGAAVAAE   60
SSTGTWTTVW TDGLTSLDRY KGRCYHIEPV AGEETQFIAY VAYPLDLFEE GSVNYMFTSI  120
VGNVFGFKAL RALRLEDLRI PAAYVKTFQG PPQGIQVERD KLNKYGRPLL GCTIKPKLGL  180
SAKNYGRAVY ECLRGGLDFT KDDENVNSQP FMRWRDRFLF CAEAIYKAQA ETGEIKGHYL  240
NATAGTCEEM MKRAVFAREL GVPIVMHDYL TVGFTANTTL AHYCRDNGLL LHIHRAMHAV  300
IDRQKNHGMH FRVLAKALRM SGGDHIHAGT VVGKLEGERD ITLGFVDLLR DDFIEKDRSR  360
GIFFTQDWVS LPGVLPVASG GIHVWHMPAL TEIFGDDSVL QFGGGTLGHP WGNAPGAVAN  420
RVALEACVQA RNEGRDLARE GNEIIREATK WSPELAAACE VWKEIKFEFP AMDN        474
```

```
SEQ ID NO: 6              moltype = AA   length = 180
FEATURE                   Location/Qualifiers
source                    1..180
                          mol_type = protein
                          organism = Medicago sativa
SEQUENCE: 6
MALISSAAVT TVNRASSAQA NLVAPFTGLK SSAGFPVTKK TNNDITSIAS NGGRVNCMQV    60
WPPVGKKKFE TLSYLPPLTE EQLAKEVEYL IRKGWIPCLE FELEKGFVYR ENHRSPGYYD   120
GRYWTMWRLP LFGATDSSQV LKELADCKAE YPDSFIRIIG FDNVRQVQCI SFIAHTPKNY   180

SEQ ID NO: 7              moltype = AA   length = 475
FEATURE                   Location/Qualifiers
source                    1..475
                          mol_type = protein
                          organism = Spinacia oleracea
SEQUENCE: 7
MSPQTETKAS VEFKAGVKDY KLTYYTPEYE TLDTDILAAF RVSPQPGVPP EEAGAAVAAE    60
SSTGTWTTVW TDGLTNLDRY KGRCYHIEPV AGEENQYICY VAYPLDLFEE GSVTNMFTSI   120
VGNVFGFKAL RALRLEDLRI PVAYVKTFQG PPHGIQVERD KLNKYGRPLL GCTIKPKLGL   180
SAKNYGRAVY ECLRGGLDFT KDDENVNSQP FMRWRDRFLF CAEALYKAQA ETGEIKGHYL   240
NATAGTCEDM MKRAVFAREL GVPIVMHDYL TGGFTANTTL SHYCRDNGLL LHIHRAMHAV   300
IDRQKNHGMH FRVLAKALRL SGGDIHISGT VVGKLEGERD ITLGFVDLLR DDYTEKDRSR   360
GIYFTQSWVS TPGVLPVASG GIHVWHMPAL TEIFGDDSVL QFGGGTLGHP WGNAPGAVAN   420
RVALEACVQA RNEGRDLARE GNTIIREATK WSPELAAACE VWKEIKFEFP AMDTV        475

SEQ ID NO: 8              moltype = AA   length = 123
FEATURE                   Location/Qualifiers
source                    1..123
                          mol_type = protein
                          organism = Spinacia oleracea
SEQUENCE: 8
MQVWPPLGLK KFETLSYLPP LTTEQLLAEV NYLLVKGWIP PLEFEVKDGF VYREHDKSPG    60
YYDGRYWTMW KLPMFGGTDP AQVVNEVEEV KKAPPDAFVR FIGFNDKREV QCISFIAYKP   120
AGY                                                                 123

SEQ ID NO: 9              moltype = AA   length = 475
FEATURE                   Location/Qualifiers
source                    1..475
                          mol_type = protein
                          organism = Chlorella vulgaris
SEQUENCE: 9
MSPQTETKAR VGFKAGVKDY RLTYYTPDYQ PKDTDILAAF RMTPQPGVPP EEAGAAVAAE    60
SSTGTWTTVW TDGLTSLDRY KGRCYDIEPV PGEENQYIAY IAYPLDLFEE GSVTNLFTSI   120
VGNVFGFKAL RALRLEDLRI PPAYVKTFQG PPHGIQVERD KLNKYGRGLL GCTIKPKLGL   180
SAKNYGRAVY ECLRGGLDFT KDDENVNSQP FMRWRDRFLF VAEAIYKSQA ETGEIKGHYL   240
NATAATAEAM MQRAECAKDL GVPIIMHDYL TGGFTANTSL SHYCRDNGLL LHIHRAMHAV   300
IDRQRNHGIT FRVLAKALRL SGGDHLHSGT VVGKLEGERE VTLGFVDLMR DDYIEKDRSR   360
GIYFTQDWVS LPGTMPVASG GIHVWHMPAL VEIFGDDACL QFGGGTLGHP WGNAPGAAAN   420
RVALEACTQA RNEGRDLARE GGDVIRAACK WSPELAAACE VWKEIKFEFE TIDTL        475

SEQ ID NO: 10             moltype = AA   length = 214
FEATURE                   Location/Qualifiers
source                    1..214
                          mol_type = protein
                          organism = Chlorella vulgaris
SEQUENCE: 10
MAALTASLVS CPVAVAAKPA RLASPAWPAS LSPRRLSPPS PRGPSQTAAA PARCSCGSPL    60
TTSSSRPSPT CPSDRRPDRQ AGRLHHPSGW TPALEFSNAE SAYVKDVANI RPTGGSASCN   120
YYDNRYWAMY KLPMFGCTDA SQVLAEIANA VKTFPDSYVR MAAFDAVRQV QTVAILVHRP   180
ASATDYRLPE NPQPLIGCTT QLERPQYCKS LANL                               214
```

SYSTEMS AND METHODS FOR MEASURING MAT DENSITY OF AQUATIC BIOMASS

CROSS-REFERENCE

This application is a continuation application of PCT Application No. PCT/US2022/076040, filed Sep. 7, 2022, which claims benefit of U.S. Provisional Application No. 63/241,627, filed on Sep. 8, 2021, which are incorporated herein by reference in its entirety.

INCORPORATION BY REFERENCE OF SEQUENCE LISTING

The instant application contains a Sequence Listing, which has been submitted via Patent Center. The Sequence Listing titled 200834-702301.xml, which was created on Mar. 7, 2024 and is 12,897 bytes in size, is hereby incorporated by reference in its entirety.

BACKGROUND

Recent shifts towards the prioritization of sustainable agricultural crops have led a need for processes offering high biomass yield and year-round productivity, even in non-arable land. For an aquatic biomass, the accuracy of measurement and regulation of mat density is important factor for yield and quality considerations. For example, an aquatic biomass floats and is often unevenly spread in a body of water, disrupting a fixed sensor's estimation of total aquatic biomass. Thus, there is a need for devices, systems and methods that allow for accurately measuring aquatic biomass in a body of water.

BRIEF SUMMARY

Provided herein are methods for measuring aquatic biomass, comprising: flowing aqueous liquid and aquatic biomass in a pond; measuring light absorption of a portion of the aquatic biomass, wherein the measuring comprises use of a measurement device, wherein the measurement device comprises: a shield, wherein the shield obstructs flow of the biomass in an area adjacent to a shield; and light intensity sensors, wherein the light intensity sensors comprise at least three light intensity sensors, wherein the light intensity sensors collect measurements of light intensity: at a comparator region located above a surface of the aqueous liquid; at a flow obstruction region located below a surface of the aqueous liquid in an area substantially free of an aquatic biomass; and at a biomass region located below a surface of the aqueous liquid; and determining a value for mass, surface area, density, or combinations thereof of the aquatic biomass in the pond. In some embodiments, the determining further comprises calculating, based on light intensity, the light absorption of a portion of the aquatic biomass. In some embodiments, the light intensity sensors comprise optical sensors. In some embodiments, the optical sensors each comprise a light meters lux meter, a UV meter, a photosynthetically active radiation (PAR) sensor, a camera, or a combinations thereof. In some embodiments, the optical sensors measure photometric units. In some embodiments, the optical sensors measure lumens per unit area. In some embodiments, the optical sensors measure lux or lumens per square meter. In some embodiments, the optical sensors comprise lux meters. In some embodiments, the optical sensors comprise light meters. In some embodiments, the camera comprises a digital camera, non-digital camera, integrated camera, single camera, dual camera, timer-specific camera, or combinations thereof. In some embodiments, the optical sensors comprise photosynthetically active radiation (PAR) sensors. In some embodiments, the light intensity sensors measure light absorption at 10 nanometers to 400 nanometers wavelength. In some embodiments, the light intensity sensors measure light absorption at 400 nanometers to 700 nanometers wavelength. In some embodiments, the light intensity sensors measure light absorption at 750 nanometers to 10,000 nanometers wavelength. In some embodiments, a light intensity differential is obtained from measurements of light intensity. In some embodiments, a light intensity differential calculated from a difference between a ratio of light intensity at a comparator region located above a surface of the aqueous liquid to light intensity at a biomass region below a surface of the aqueous liquid in an area not substantially free of an aquatic biomass, and a ratio of light intensity at a comparator region located above a surface of the aqueous liquid to light intensity at a biomass region below a surface of the aqueous liquid in an area in that is substantially free of an aquatic biomass. In some embodiments, the light absorption is calculated from the light intensity differential. In some embodiments, an aquatic biomass measurement is related to the measurement of light absorption. In some embodiments, the measurement is density. In some embodiments, the measurement is value of mass. In some embodiments, the measurement is surface area. In some embodiments, the flow is a circulating flow. In some embodiments, the method comprises the use of one, two, three, four, five, or more measurement devices. In some embodiments, the light intensity sensors to collect measurements of light intensity communicate data measurements to an imaging system or a computer system adapted to process the data, wherein the processing comprises calculations. In some embodiments, the value for mass, surface area, density, or combinations thereof of the aquatic biomass in the pond is determined from one or more device. In some embodiments, the aquatic biomass comprises *Lemna minor*. In some embodiments, the aquatic biomass comprises an aquatic photosynthetic organism. In some embodiments, the aquatic photosynthetic organism comprises a member of the Bacillariophyta, Chlorophyta, Chrysophyta, Euglenophyta, Euglenozoa, Paeophyta, *Porphyra*, Pyrrophyta, Rhodophyta, or Xanthophyta phylum, or combinations thereof. In some embodiments, the aquatic photosynthetic organism comprises a member of the Caulerpaceae, Chlorophyta, Chrysophyta, Chrysophyceae, Cryptophyceae, Dinophyceae, Euglenophyceae, Fucaceae, Florideophyceae, Gigartinaceae, Gracilariaceae, Laminariaceae, Lemnaceae, Salviniaceae, Monostromataceae, Phaeophyceae, Ulvaceae, Xanthophyceae, or algae family, or combinations thereof. In some embodiments, the aquatic photosynthetic organism comprises a member of the *Ankistrodesmus, Asteromonas, Azolla, Carteria, Chlamydomonas, Chlorella, Chlorococcum, Chlorogonium,* Chlorophyceace, *Chrysosphaera, Dunaliella, Euglena, Fucus, Furcellaria, Gracilaria, Haematococcus, Laminaria, Landoltia, Lemna, Macrocystis, Monoraphidium, Monostroma, Nannochloropsis, Neochloris, Oedogonium, Ochromona, Oscillatoria, Pelagomonas, Phormidium, Pleurococcus, Porphyra, Pyrobotrys, Sargassum, Scenedesmus, Selenastrum, Spirodela, Spirulina, Volvox, Wolffia,* or *Wolffiella* genus, or combinations thereof. In some embodiments, the aquatic photosynthetic organism comprises *Lemna*. In some embodiments, the *Lemna* comprises *Lemna aequinoctialis, Lemna disperma, Lemna ecuadoriensis, Lemna gibba, Lemna japonica, Lemna minuta,*

*Lemna obscura, Landoltia punctata, Lemna perpusilla, Lemna tenera, Lemna trisulca, Lemna turionifera, Lemna valdiviana, Lemna yungensis, Spirodela polyrhiza, Wolffia arrhiza, Wolffia globosa*. In some embodiments, the aquatic photosynthetic organism comprises *Azolla, Azolla caroliniana, Azolla cristata, Azolla filiculoides, Azolla imbricata, Azolla nilotica, Azolla pinnata, Azolla rubra*, or combinations thereof. In some embodiments, the aquatic photosynthetic organism comprises *Ascophyllum nodosum, Botrydium, Caulerpa, Chondrus crispus*, Euglenoids, *Fucus, Fucus crispus, Fucus serratus, Fucus vesiculosus, Furcellaria lumbricalis, Gracilaria parvispora, Gracilaria tikvahiae, Laminaria digitata, Laminaria farlowii, Laminaria hyperborean, Laminaria nigripes, Macrocystis pyrifera, Monostroma kuroshiense, Monostroma latissimum, Monostroma nitidum, Prymnesium parvum, Palmaria palmata, Saccharina latissima, Tribonema, Ulva intestinalis, Vaucheria*, or combinations thereof. In some embodiments, the aquatic photosynthetic organism comprises duckweed, duckweed fern, mosquito fern, water fern, fairy moss, and algae, or combinations thereof. In some embodiments, the aquatic photosynthetic organism comprises lesser duckweed, minute duckweed, gibbous duckweed, common duckweed, ivy duckweed, least duckweed, Valdivia duckweed, rockweed, gutweed, green algae, golden algae, golden brown algae, golden brown algae and diatoms, fire algae, red algae, yellow-green algae, brown algae, single-cell algae, microalgae, macroalgae, kombu, kelp, sugarkelp, grass kelp, giant kelp, bladder kelp, sea oak, knotted kelp, knotted wrack, sea lettuce, serrated wrack, carrageen, forked seaweed, brown seaweed, dulse, dulce sol, or combinations thereof. In some embodiments, the aquatic photosynthetic organism comprises a floating aquatic photosynthetic organism. In some embodiments, the density comprises mat density. In some embodiments, mat density is from about 750 g/m$^2$ to about 1500 g/m$^2$. In some embodiments, the floating aquatic photosynthetic organism comprises a *Lemna* species. In some embodiments, the aquatic biomass comprises a thickness of about 0.1 millimeters to about 5 millimeters. In some embodiments, the aquatic biomass comprises a weight of about 100 grams per meter squared to about 3000 grams per meter squared.

Provided herein are methods for measuring aquatic biomass, the methods further comprising: the step of optimizing a growth of the aquatic biomass, wherein the method comprises adjusting a mass, surface area, or density, of the aquatic biomass based on the calculated mass, surface area, or density, thereby optimizing the growth of the aquatic biomass or aquatic photosynthetic organism. In some embodiments, optimizing the growth of the aquatic biomass comprises adjusting aquatic biomass over a time interval. In some embodiments, optimizing the growth of the aquatic biomass comprises adjusting aqueous liquid turbidity. In some embodiments, optimizing the growth of the aquatic biomass comprises adjusting temperature, pH, nutrients, flow, light intensity, light spectrum, and time interval. In some embodiments, the method further comprises harvesting the aquatic biomass.

Provided herein are methods for harvesting aquatic biomass from aqueous liquid, comprising: measuring light intensity of a portion of the aquatic biomass, wherein the measuring comprises use of a measurement device; determining a value for mass, surface area, density, or combinations thereof of the portion of the aquatic biomass; obstructing a portion of the aquatic biomass with a harvesting unit upon reaching a targeted value for mass, surface area, density, or combinations thereof of the portion of the aquatic biomass; and removing a portion of the aquatic biomass from the aqueous liquid. In some embodiments, the determining further comprises calculating, based on the measurements of light intensity, a light absorption of a portion of the aquatic biomass. In some embodiments, harvesting the aquatic biomass involves removing a portion of the aquatic biomass from the aqueous liquid about once a day to about once every 14 days. In some embodiments, harvesting the aquatic biomass involves use of a water draining unit for removing a portion of the aquatic biomass from the aqueous liquid. In some embodiments, the water draining unit is a net. In some embodiments, the net is a net bag, a hoop net, a scoop net, a tubular net, a mesh net, a fishing net, a drive-in net, a mounted net, or a combinations thereof.

Provided herein are methods of plant protein production, the method comprising: measuring light absorption of a portion of an aquatic biomass, wherein the measuring comprises use of a measurement device; determining a value for mass, surface area, density, or combinations thereof of the portion of the aquatic biomass; and harvesting the aquatic biomass upon reaching a targeted value for mass, surface area, density, or combinations thereof of the portion of the aquatic biomass. In some embodiments, the calculating further comprises determining, based on the measurements of light intensity, a light absorption of a portion of the aquatic biomass. In some embodiments, the harvesting further comprises removing a portion of the aquatic biomass from an aqueous liquid. In some embodiments, the harvesting further comprises isolating the plant protein from the portion of the aquatic biomass to produce plant protein isolate. In some embodiments, the desired value for density is mat density. In some embodiments, mat density is from about 750 g/m$^2$ to about 1500 g/m$^2$. In some embodiments, the plant protein isolate is extracted from a *Lemna* species. In some embodiments, the plant protein isolate comprises RuBisCo. In some embodiments, the plant protein isolate is a soluble protein powder. In some embodiments, the plant protein isolate is a white, odorless, and soluble protein powder.

Provided herein are devices for aquatic biomass measurement, the device comprising: a shield for obstructing a flow of an aquatic biomass in an area adjacent to the shield; and at least three sensors to collect measurements of light intensity at a comparator region located above a surface of the aqueous liquid, at a flow obstruction region located below a surface of the aqueous liquid in an area substantially free of an aquatic biomass, and at a biomass region located below a surface of the aqueous liquid. In some embodiments, the at least three sensors comprise optical sensors. In some embodiments, the optical sensors each comprise a light meter, a lux meter, a UV meter, a photosynthetically active radiation (PAR) sensor, a camera, or a combinations thereof. In some embodiments, the optical sensors measure photometric units. In some embodiments, the optical sensors measure photometric units once over a time interval of about 30 seconds to about 10 minutes. In some embodiments, the optical sensors measure lumens per unit area. In some embodiments, the optical sensors measure lux or lumens per square meter. In some embodiments, the optical sensors measure lumens per square meter from about 0 lux to about 75,000 lux. In some embodiments, the optical sensors measure lumens per square meter at a temperature of about 1° C. to about 45° C. In some embodiments, the optical sensors measure lumens per square meter at a temperature of about 10° ° C. to about 40° C. In some embodiments, the optical sensors comprise lux meters. In some embodiments, the optical sensors comprise light meters. In some embodiments, the at least three sensors comprise a digital camera, a non-digital camera, an integrated camera, a single camera, a dual camera, a timer-specific camera, or a combinations thereof. In some embodiments, the at least three sensors comprise a camera with a depth of at least 10 bits per pixel. In some embodiments, the optical sensors comprise photosynthetically active radiation (PAR) sensors. In some embodiments, the light intensity sensors measure light absorption at 10 nanometers to 400 nanometers wavelength. In some embodiments, the light intensity sensors measure light absorption at 400 nanometers to 700 nanometers wavelength. In some embodiments, the light intensity sensors measure light absorption at 750 nanometers to 10,000 nanometers wavelength. In some embodiments, the at least three sensors comprise configuration to communicate with one or more processing units. In some embodiments, the device comprises configuration to communicate with one or more processing units. In some embodiments, the device further comprises at least three arms. In some embodiments, each of the at least three sensors comprise configuration to be positioned on one of the at least three arms. In some embodiments, one of the at least three arms comprise configuration to be connected to a sensor, a shield, a frame, or combinations thereof. In some embodiments, the one or more arms comprise configuration to be connected to a frame. In some embodiments, the shield comprises at least one wall that obstructs a portion of the aquatic biomass. In some embodiments, the at least one wall keeps the aquatic biomass from contacting an optical sensor. In some embodiments, the shield comprises a base. In some embodiments, the at least one wall is u-shaped. In some embodiments, the at least one wall comprises a vent. In some embodiments, the device, frame, arms, shield, or at least one of the at least three sensors comprise configuration to be anchored to a bottom of a pond. In some embodiments, the device, frame, arms, shield, or at least one of the at least three sensors comprise configuration to be floating on an aqueous liquid in a pond. In some embodiments, the device comprises metal, plastic polymer, copper, galvanized iron, polyvinyl chloride (PVC), or combinations thereof. In some embodiments, the device comprises a light source.

Provided herein are systems for aquatic biomass measurement, the systems comprising: a pond; an aqueous liquid in a pond; an aquatic biomass; at least one measurement device; one or more processing units; and one or more user interface. In some embodiments, the measurement device comprises configuration to be communicatively coupled to a one or more processing unit. In some embodiments, the one or more processing unit comprises configuration to be communicatively coupled to one or more user interface. In some embodiments, the one or more processing units comprises a receiver. In some embodiments, the one or more processing unit comprises a transmitter. In some embodiments, the one or more processing unit comprises a central processing unit. In some embodiments, the one or more user interface comprises an output device. In some embodiments, the one or more user interface comprises an input device. In some embodiments, the output device comprises a screen. In some embodiments, the input device comprises a keyboard and a mouse. In some embodiments, the one or more processing units are configured to calculate light absorption from light intensity measurement data. In some embodiments, the one or more processing units are configured to determine a value for mass, surface area, density, or combinations thereof of the aquatic biomass in the pond from the light absorption calculation. In some embodiments, the user interface is configured to receive a determined value for mass, surface area, density, or combinations thereof of the aquatic biomass in the pond from the processing units. In some embodiments, the pond is configured to hold aqueous liquid at depth of 10 centimeters to about 50 centimeters. In some embodiments, the pond is configured to hold aqueous liquid at a temperature of about 1° C. to about 45° C. In some embodiments, the pond is configured to hold aqueous liquid at a temperature of about 10° C. to about 40° C. In some embodiments, the pond is configured to hold aqueous liquid at a pH of about 4 to about 8.5. In some embodiments, the pond is configured to hold aqueous liquid at a pH of about 5 to about 7. In some embodiments, the system is fully automatic. In some embodiments, the system is partially automatic. In some embodiments, the system is not automatic. In some embodiments, the systems further comprising a propulsion mechanism, wherein a propulsion mechanism comprises configuration to propel the circulating aqueous liquid at a flow rate. In some embodiments, the propulsion mechanism comprises a paddle wheel or a pump. In some embodiments, the aqueous liquid is a circulating aqueous liquid, wherein the circulating aqueous liquid comprises a flow rate of about 0.01 meters/second to about 1 meter/second. In some embodiments, the pond has a depth of about 10 centimeters to about 50 centimeters. In some embodiments, the pond is a container. In some embodiments, the pond is a watertight container. In some embodiments, the pond is a container comprising an open top surface, or peripheral walls and a base. In some embodiments, the pond is plastic lined. In some embodiments, the pond is a raceway-shaped pond. In some embodiments, the systems comprise a cover and wherein the pond is at least partially covered with the cover.

Provided herein are systems for optimizing biomass growth, the systems comprising systems for aquatic biomass measurement, wherein the processing units is configured to establish inoculation or harvest required to optimize aquatic biomass growth based on measurement data. In some embodiments, the system further comprises a harvesting unit. In some embodiments, the harvesting unit comprises an obstruction pipe. In some embodiments, the obstruction pipe is a polyvinyl chloride (PVC) pipe. In some embodiments, the obstruction pipe has a diameter of at least the thickness of the aquatic biomass. In some embodiments, the obstruction pipe has a diameter of about 4 inches to about 6 inches. In some embodiments, the system further comprises an inoculation unit. In some embodiments, the inoculation unit is a net. In some embodiments, the net is a net bag, a hoop net, a scoop net, a tubular net, a mesh net, a fishing net, a drive-in net, a mounted net, or combinations thereof.

Provided herein are systems for maximizing protein harvest, the systems comprising systems for aquatic biomass measurement, wherein the system further comprises a harvesting unit. In some embodiments, the systems are for *Lemna minor* measurement. In some embodiments, the systems are for optimizing *Lemna minor* growth. In some embodiments, the systems are for maximizing protein harvest from *Lemna minor*.

BRIEF DESCRIPTION OF THE DRAWINGS

The features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
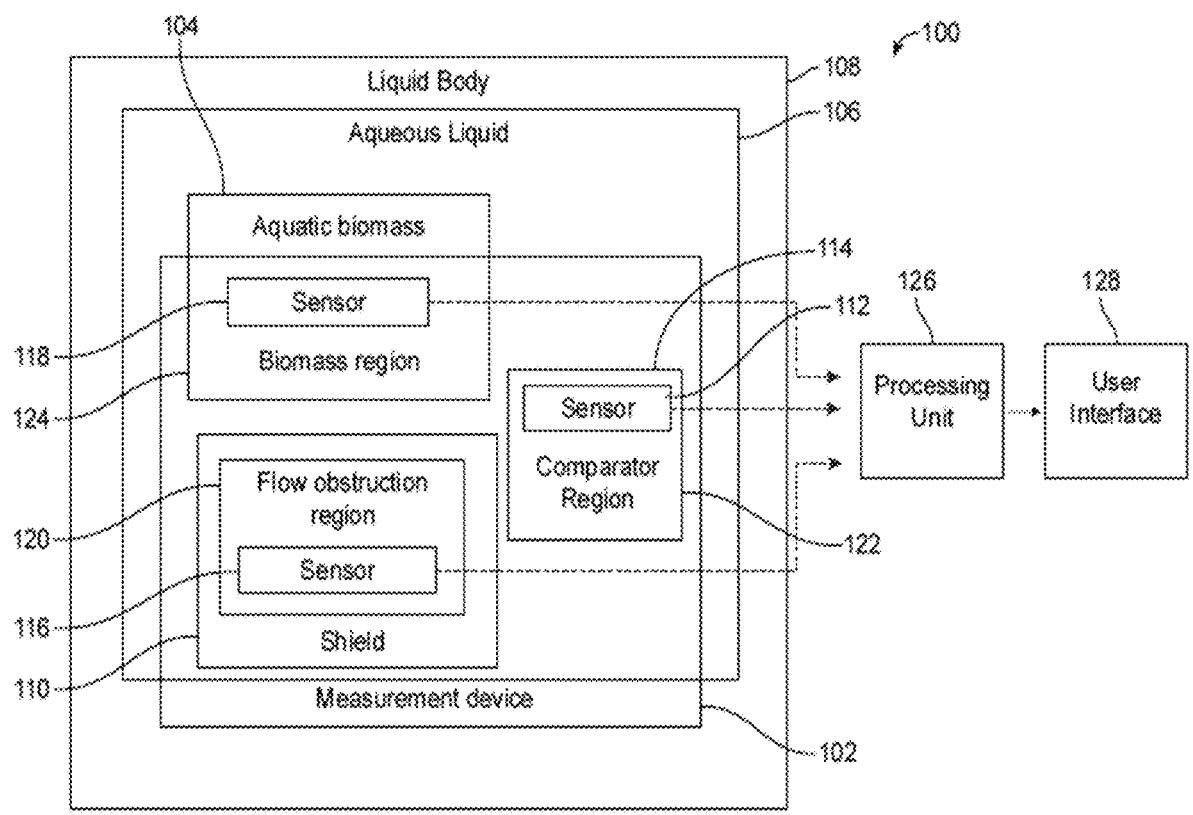
FIG. 1 illustrates a schematic view of one embodiment of a system for providing a measurement of an aquatic biomass in accordance with aspects of the present subject matter. Such a system can comprise the use of a measurement device as shown in FIG. 2 which includes three or more light intensity sensors, each configured to measure light intensity values of light as it is passing through an aquatic biomass and/or through a background medium. The aquatic biomass can be or include *Lemna minor*. The background medium can include aqueous liquid or air.

Described herein are systems, devices, and methods for measuring an aquatic biomass. Such innovations allow for enhanced growth, monitoring, yield, and quality of the biomass and/or resultant purification products, including protein isolate compositions.

Definitions

Unless defined otherwise, all technical and scientific terms used herein have the same meaning as commonly understood by those of ordinary skill in the art to which embodiments herein belongs. The following definitions are provided to facilitate understanding of certain terms used frequently herein and are not meant to limit the scope of the present disclosure.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein can be for the purpose of describing particular embodiments only and is not intended to be limiting.

Herein, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Unless specifically stated or obvious from context, as used herein, the term "about" as used herein when referring to a measurable value such as a dosage or time period and the like refers to variations of ±20%, ±10%, ±5%, ±1%, ±0.5%, or even ±0.1% of the specified amount. As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Herein, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

Reference herein to "some embodiments," "an embodiment," "one embodiment" or "other embodiments" means that a particular feature, structure, or characteristic described in connection with the embodiments can be included in at least some embodiments, but not necessarily all embodiments, of the present disclosure.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps. It is contemplated that any embodiment discussed in this specification can be implemented with respect to any method or composition of the present disclosure, and vice versa. Furthermore, compositions of the present disclosure can be used to achieve methods of the present disclosure.

As used herein, "identity," refers to a relationship between two or more amino acid sequences, as determined by comparing the sequences. In the art, "identity" also refers to the degree of sequence relatedness between amino acid sequences as determined by the match between strings of such sequences. "Identity" can be readily calculated by known methods, including, but not limited to, those described in (Computational Molecular Biology, Lesk, A M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453) algorithm (e.g., NBLAST, and XBLAST). The default parameters are used to determine the identity for the polypeptides of the present disclosure, unless stated otherwise.

Ranges of values are disclosed herein. The ranges set out a lower limit value and an upper limit value. Unless otherwise stated, the ranges include the lower limit value, the upper limit value, and all values between the lower limit value and the upper limit value, including, but not limited to, all values to the magnitude of the smallest value (either the lower limit value or the upper limit value) of a range. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of about 0.1% to about 5%" should be interpreted to include not only the explicitly recited values of about 0.1% to about 5%, but also, unless otherwise stated, include individual values (e.g., about 1%, about 2%, about 3%, about 4%, etc.) and the sub-ranges (e.g., about 0.5% to about 1.1%; about 0.5% to about 2.4%; about 0.5% to about 3.2%, about 0.5% to about 4.4%, and other possible sub-ranges, etc.) within the indicated range. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about, it will be understood that the particular value forms a further disclosure. For example, if the value "about 10" is disclosed, then "10" is also disclosed.

As used herein, the term "substantially free" refers to less than 5% of a measurable value.

Methods and Systems for Aquatic Biomass Measurement

Provided herein are methods and systems for measuring an aquatic biomass described herein. In some embodiments, methods and systems for measuring an aquatic biomass comprise the use of: an aqueous liquid and an aquatic biomass in the aqueous liquid, and one or more measurement devices described herein. In some embodiments, the one or more measurement device measures light absorption, optionally of a portion of the aquatic biomass. In some embodiments, the one or more measurement device comprises: a shield and one or more light intensity sensors, wherein each one or more light intensity sensors collects a measurement of light intensity. In some embodiments, one or more light intensity sensors collect a measurement of light intensity at one or more of: an area above a surface of an aqueous liquid, an area below the surface of the aqueous liquid in an area that is not substantially free of an aquatic biomass, an area below the surface of then aqueous liquid in an area substantially free of an aquatic biomass, or combinations thereof. In some embodiments, an area above a surface of the aqueous liquid may be referred to herein as a comparator region. In some embodiments, an area below a surface of the aqueous liquid in an area that is not substantially free of an aquatic biomass may be referred to herein as a biomass region. In some embodiments, an area below a surface of an aqueous liquid in an area substantially free of an aquatic biomass may be referred to herein as a flow obstruction region. In some embodiments, one or more light intensity sensors collect a measurement of light intensity at one or more of: a comparator region, a biomass region, a flow obstruction region, or combinations thereof.

In some embodiments, methods and systems described herein further comprise calculating based on the measurements of light intensity, the light absorption of a portion of the aquatic biomass. In some embodiments, systems and methods described herein further comprise determining, based on the measurement of light absorption, a value for mass, surface area, density, or combinations thereof of the aquatic biomass in a body of liquid. In some embodiments, systems and methods described herein further comprise the use of one or more processing units. In some embodiments, systems and methods described herein further comprise the use of one or more user interfaces.

Referring to the drawings: FIG. 1 illustrates a schematic view of an exemplary workflow of a system 100 for a measurement of an aquatic biomass in accordance with aspects of the present subject matter. In general, a system 100 will be described with reference to measurement device 102 described herein with reference to FIG. 2. Additionally, it should be appreciated that, for purposes of illustration, communicative links or electrical couplings of a system 100 shown in FIG. 1 are indicated by dashed arrows.

As shown in FIG. 1, the system 100, comprises an aquatic biomass 104 and an aqueous liquid 106. The aquatic biomass 104 may generally be suspended in or floating on an aqueous liquid 106, both of which may be contained in a liquid body 108. In some embodiments, a liquid body is in a pond. The system 100, and specifically, the measurement device 102 comprises a shield 110. The system 100, and specifically, the measurement device 102 further comprises one or more sensors 112, such as a first sensor 114, a second sensor 116, and a third sensor 118.

In some instances, the shield 110 is capable of dispersing an amount of an aquatic biomass 104, and in some cases obstruct a flow of aquatic biomass 104, thereby rendering a flow obstruction region 120 which is substantially free of aquatic biomass 104. In some instances, a first sensor 114 measures light intensity at a comparator region 122 that is located above a surface of the aqueous liquid 106. In some instances, a second sensor 116 measures light intensity at a flow obstruction region 120 that adjacent to a shield 110 and located below a surface of an aqueous liquid 106 in an area substantially free of an aquatic biomass 104. In some instances, a third sensor 118 measures light intensity at a biomass region 124 that located below a surface of an aqueous liquid 106 and in an area that comprises an aquatic biomass 104.

As additionally shown in FIG. 1, the system 1 may include one or more processing units 126 configured to be communicatively coupled to the one or more sensors 112, and at least one user interface 128 configured to be communicatively coupled to one or more processing units 126. The at least one user interface 128 described herein may include, without limitation, any combination of input and/or output devices that allow a user to provide operator inputs to one or more processing units 126 and/or that allow the one or more processing units 126 to provide feedback to the user, such as a keyboard, keypad, pointing device, buttons, knobs, touch sensitive screen, mobile device, audio input device, audio output device, and/or the like.

Figure 2:
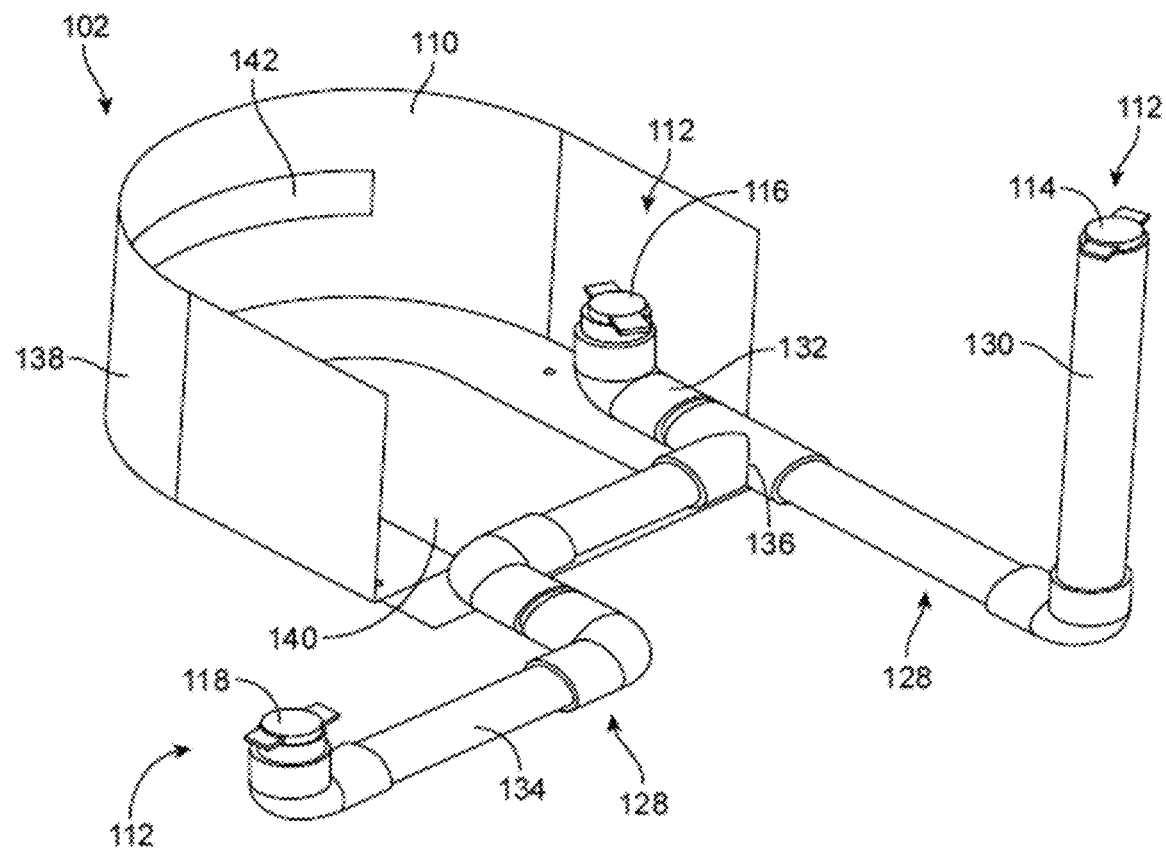
FIG. 2 illustrates a perspective view of one embodiment of a measurement device in accordance with some aspects of the present subject matter.

FIG. 2 illustrates a perspective view of one embodiment of a measurement device 110 in accordance with aspects of the present subject matter. Specifically, FIG. 2 illustrates a perspective view of a measurement device 102 including: a shield 110 and three one or more light intensity sensors 12 (i.e., a first light intensity sensor 114, a second light intensity sensor 116, a third light intensity sensor 118). Each light intensity sensor comprises configuration to measure light intensity as it passes through an aquatic biomass and/or through a background medium. The background medium can include aqueous liquid (e.g., water), or air.

As shown in FIG. 2, a measurement device may comprise one or more arms 128, such as three arms (e.g., a first arm 130, a second arm 132, a third arm 134) wherein the one or more arms support the one or more light intensity sensors 112 (e.g., a first light intensity sensor 114, a second light intensity sensor 116, a third light intensity sensor 118 supported by a first arm 130, a second arm 132, a third arm 134, respectively). In some embodiments, each arm 128 comprises configuration to be connected to a light intensity sensor, a shield, and/or a frame 136. Further shown in FIG. 2, a shield 110 may comprise at least one wall (138), which may be u-shaped, may extend laterally and can obstruct a flow of an aqueous liquid. As shown in FIG. 2, the shield 110 may comprise a base 140 which can support at least one wall 138. The shield 110 may comprise a vent 142, which can be affixed into at least one wall 138. The measurement device 102 may also comprise a frame 136 configured to support the base 140 and/or the three one or more arms 128.

Figure 3:
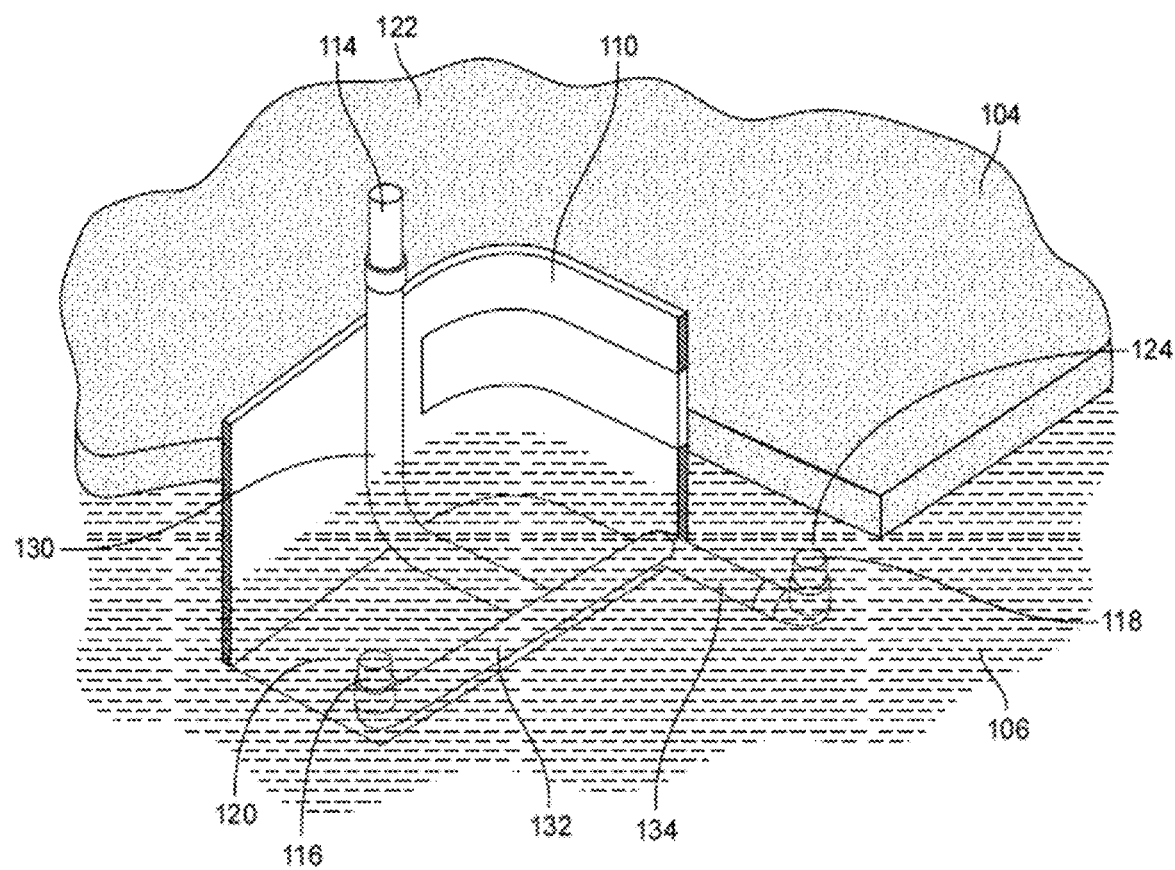
FIG. 3 illustrates a cross-section view of one embodiment of a system for providing a measurement of an aquatic biomass in accordance with aspects of the present subject matter.

FIG. 3 illustrates a cross-section view of one embodiment of a system 100 for a measurement of an aquatic biomass in accordance with aspects of the present subject matter. In general, a system 100 will be described with reference to measurement device 102 described above with reference to FIG. 2, and the system of FIG. 1.

As shown in FIG. 3, the system comprises an aquatic biomass 104, an aqueous liquid 106, and a measurement device 102 as shown in FIG. 2 which includes a shield 110 and a first light intensity sensor 114, a second light intensity sensor 116, a third light intensity sensor 118 supported by a first arm 130, a second arm 132, a third arm 134, respectively. A first light intensity sensor 114 is configured to measure light intensity at a comparator region 122, which is above a surface of an aqueous liquid 106. A second light intensity sensor 116 is configured to measure light intensity at a flow obstruction region 120, which is located below a surface of an aqueous liquid and at an area which is substantially free of aquatic biomass. A third light intensity sensor 118 is configured to measure light intensity at a biomass region 124, which is below a surface of aqueous liquid at an area comprising an aquatic biomass 104.

Figure 4:
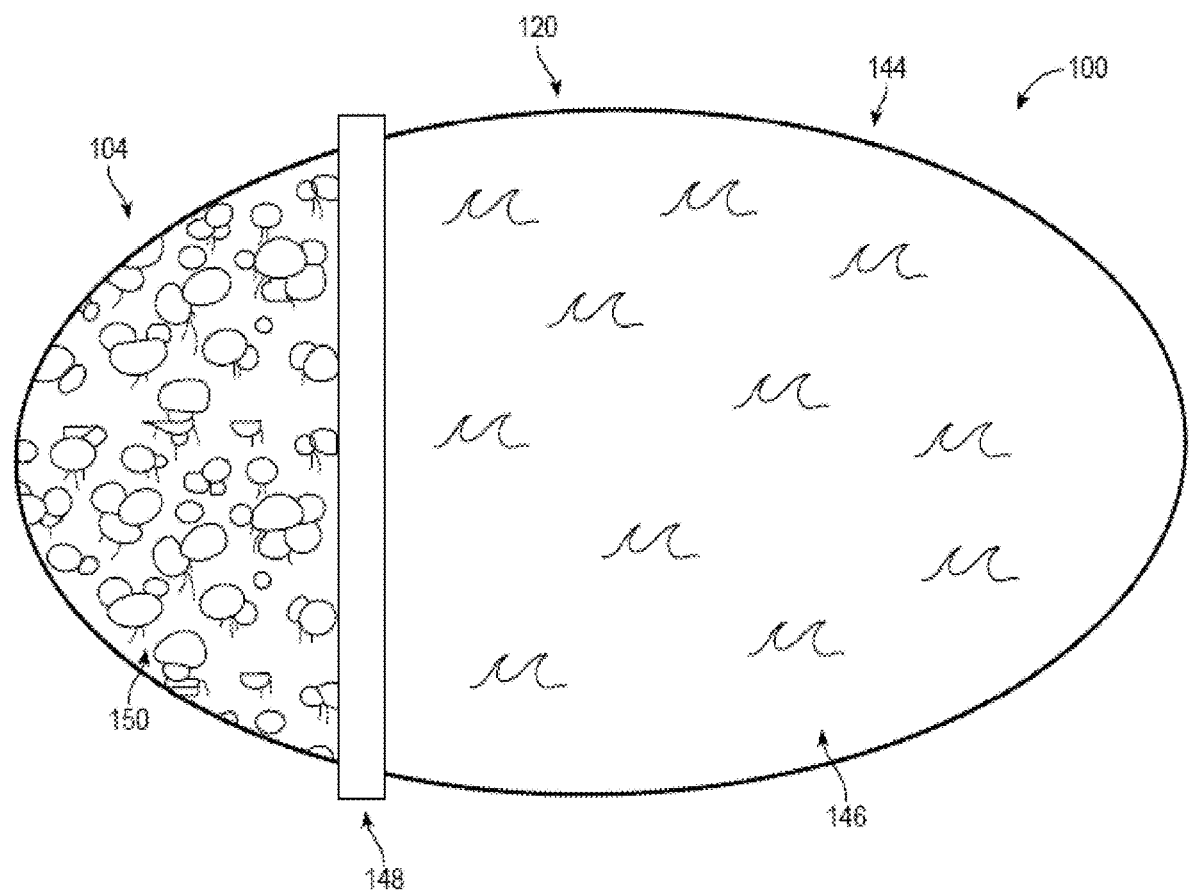
FIG. 4 illustrates a schematic of another embodiment of a system for aquatic biomass measurement in accordance with an embodiment of the present invention.

Illustrated in FIG. 4 is a schematic of another embodiment of a system 100 for a measurement of an aquatic biomass in accordance with aspects of the present subject matter. In some embodiments, a body of liquid is a pond 144 and the aqueous liquid is water 146. In some embodiments, a shield is an obstruction device 148 located in an area in the water 146 to generate a flow obstruction region 120 which is substantially free of aquatic biomass. In some embodiments, an aquatic biomass is Lemna 150.

Figure 5:
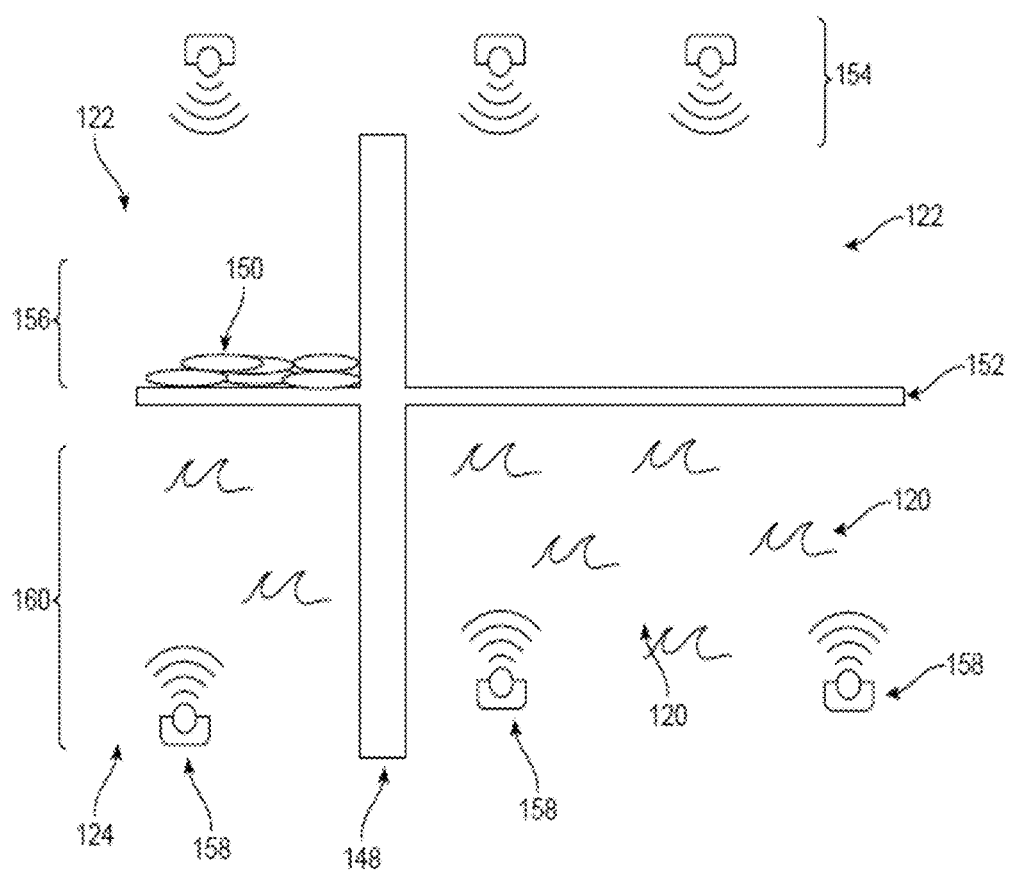
FIG. 5 illustrates a schematic diagram of an additional embodiment of a system for aquatic biomass measurement in accordance with an embodiment of the present invention.

FIG. 5 depicts a schematic diagram of yet another embodiment for a measurement of an aquatic biomass in accordance with aspects of the present subject matter. In some embodiments, systems provided herein comprise a pond, wherein the pond has a surface 152, the use of a first set of light intensity sensors 154 located above a surface of the aqueous liquid 156, a second set of light intensity sensors 158 located below a surface of a aqueous liquid 160, and an obstruction device 148 to generate a flow obstruction region 120 in the water 146 which is substantially free of Lemma 150.

Figure 6:
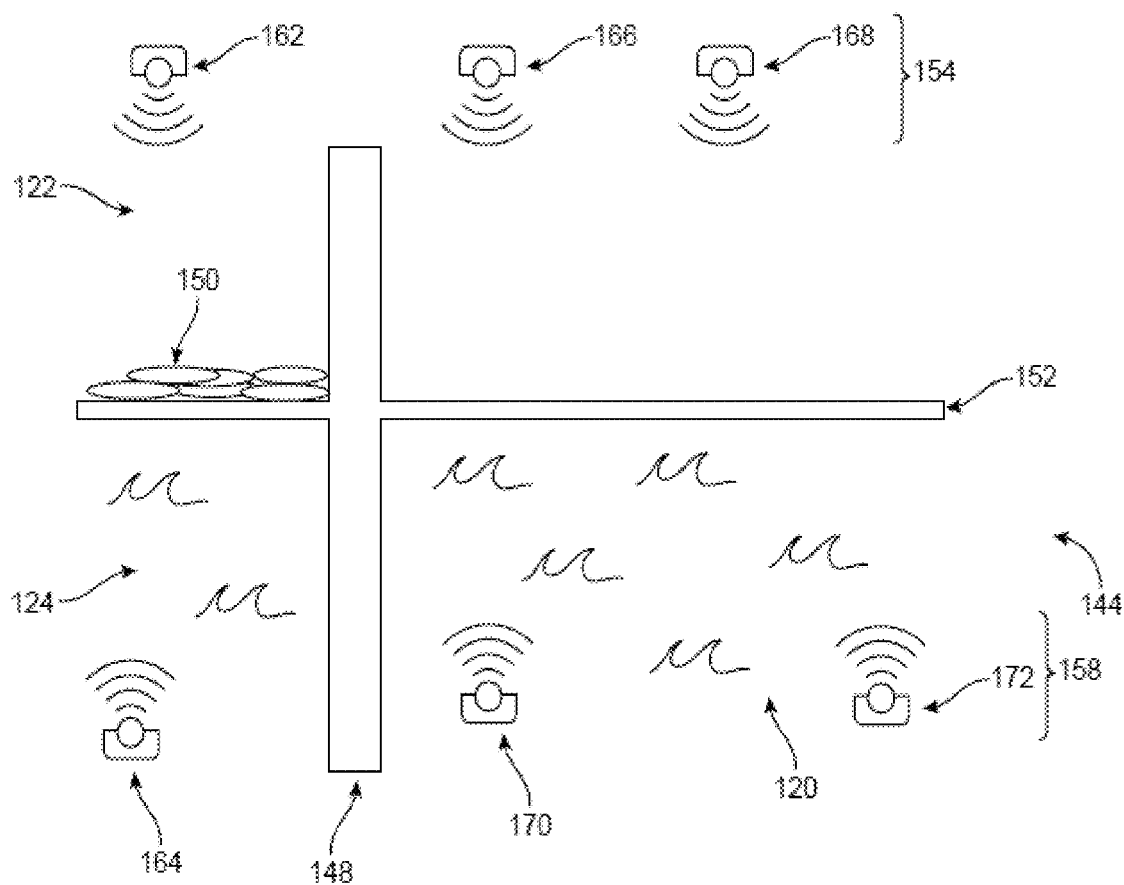
FIG. 6 illustrates a schematic diagram of a further embodiment of a system for aquatic biomass measurement in accordance with an embodiment of the present invention.

Referring to FIG. 6, a schematic diagram of an additional embodiment for a measurement of an aquatic biomass is illustrated in accordance with aspects of the present subject matter. Systems described in such embodiments may be described in reference to the system of FIG. 5. In some embodiments, systems described herein comprise a first subset 162 of a first set of sensors 154 and a first subset 164 of the second set of sensors 158, wherein said subsets are located in the area upstream from the obstruction device 148. In some embodiments, systems described herein comprise a second subset 166 and 168 of a first set of sensors 154 and a second subset 170 and 172 of a second set of sensors 158, wherein said subsets are located in other locations in the pond 144.

Figure 7:
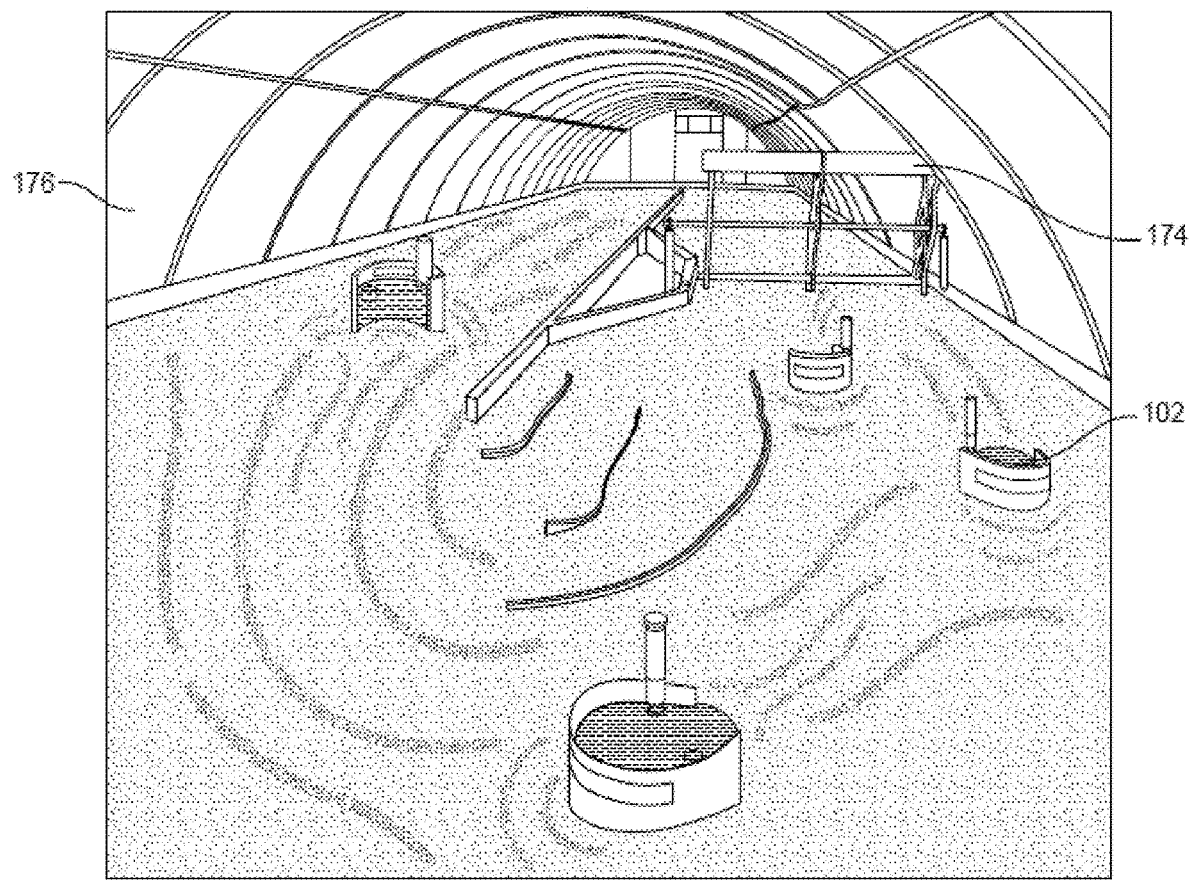
FIG. 7 illustrates a perspective view of yet another embodiment of a system for providing measurement of an aquatic biomass in accordance with some aspects of the present subject matter.

Referring to FIG. 7, a perspective view of one embodiment of a system 100 for a measurement of an aquatic biomass is illustrated in accordance with aspects of the present subject matter. In general, a system 100 will be described with reference to the figures herein. Additionally, it should be appreciated that, for purposes of illustration, an aqueous liquid 106 may be a flowing or a circulating aqueous liquid and is indicated by darker shading. In some embodiments, systems described herein may further comprise a propulsion mechanism 174 to propel the circulation of the aqueous liquid 106.

As shown in FIG. 7, in some embodiments, a system may comprise more than one measurement devices, for example four measurement devices 102 positioned in various locations in the body of liquid 108. It is contemplated that such a system may be useful for determining optimal locations of measurement devices in a pond, or for providing multiple data points, the statistical average of which can be used to determine an aquatic biomass measurement (e.g., mat density) or both. In some embodiments, a system may further comprise a covering 176, which may be a partial covering or a full covering. In some embodiments, measurement devices are floating or fixed. In some embodiments, some measurement devices are floating in an aqueous liquid, and some measurement devices are fixed or anchored to the bottom of the body of liquid. In some embodiments, measurement devices are placed according to the flow of an aqueous liquid propelled by the propulsion mechanism described herein.

Body of Liquid

Systems and methods described herein comprise a body of liquid or a use thereof. Bodies of liquid described herein generally comprises a container that functions to hold the aqueous liquid. Aquatic biomass measured herein is cultivated in the body of liquid. In some embodiments, a container has an open top surface. In some embodiments, a container comprises one or more of an open top surface, or peripheral walls and a base. In some embodiments, a container comprises three peripheral walls, and a base. In some embodiments, a container comprises three peripheral walls connected to a base. In some embodiments, a container does not have an open top surface (i.e., is enclosed). A container is generally capable of housing conditions necessary to cultivate an aquatic biomass (e.g., abiotic and biotic factors). Exemplary conditions to foster cultivation of an aquatic biomass are described herein. A container may be any suitable container. In some embodiments, a container comprises a watertight container. In some embodiments, a container comprises watertight lining. In some embodiments, a container plastic lining. In some embodiments, a container comprises configuration to be an oblong shape. In some embodiments, a container comprises configuration to be an elongated oval shape. In some embodiments, a container comprises configuration to be a raceway shape. In some embodiments, the body of liquid comprises a pond or tank. In some embodiments, the body of liquid is a sub section of a lake, ocean, river or similar environment having a delineated barrier to create a spatially limited controlled cultivation volume.

In some embodiments, a body of liquid comprises configuration to be about 10 cm to about 10 m, or more, deep. In some embodiments, a body of liquid comprises configuration to be about 10 cm, about 100 cm, about 500 cm, about 1 m, about 2 m, about 3 m, about 4 m, about 5 m, about 6 m, about 7 m, about 8 m, about 9 m, about 10 m or more.

In some embodiments, a body of liquid comprises configuration to be about 5 m to about 500 m, or more, in a longest dimension. In some embodiments, a body of liquid comprises configuration to be about 5 m, about 50 m, about 100 m, about 200 m, about 300 m, about 400 m, about 500 m or more.

In some embodiments, a body of liquid comprises configuration to have a surface area about 10 $m^2$ to about 10,000 $m^2$, or more, in a longest dimension. In some embodiments, a body of liquid comprises configuration to be about 10 $m^2$, about 100 $m^2$, about 500 $m^2$, about 1,000 $m^2$, about 2,000 $m^2$, about 3,000 $m^2$, about 4,000 $m^2$, about 5,000 $m^2$, about 6,000 $m^2$, about 7,000 $m^2$, about 8,000 $m^2$, about 9,000 $m^2$, about 10,000 $m^2$ or more.

In some embodiments, a body of liquid comprises configuration to contain an aqueous liquid at a temperature of about 1° ° C. to about 45° C. In some embodiments, a body of liquid comprises configuration to contain an aqueous liquid at a temperature of about 10° C. to about 40° C. In some embodiments, a body of liquid comprises configuration to contain an aqueous liquid at a pH of about 2 to about 11. In some embodiments, a body of liquid comprises configuration to contain an aqueous liquid at a pH of about 4 to about 8. In some embodiments, a body of liquid comprises configuration to contain an aqueous liquid at a pH of about 4, about 4.1, about 4.2, about 4.3, about 4.4, about 4.5, about 4.6, about 4.7, about 4.8, about 4.9, about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.1, about 8.2, about 8.3, about 8.4, or about 8.5, or more.

In some embodiments, a body of liquid comprises configuration to contain a circulating aqueous liquid. In some embodiments, a body of liquid comprises configuration to contain a flowing aqueous liquid. In some embodiments, a body of liquid comprises configuration to contain a flowing and circulating aqueous liquid. In some embodiments, a body of liquid comprises configuration to hold an aqueous liquid flowing at a rate of about 0.01 meters/second to about 1 meters/second. In some embodiments, systems and methods described herein comprise a propulsion mechanism wherein a propulsion mechanism comprises configuration to propel an aqueous liquid. In some embodiments, a propulsion mechanism propels an aqueous liquid at a flow rate. In some embodiments, a propulsion mechanism comprises configuration to propel an aqueous liquid at a flow rate. In some embodiments, a flow rate of a flowing liquid is about 0.01 meters/second to about 1 meters/second. In some embodiments, a flow rate of a flowing liquid is about 0.01 meters/second to about 0.5 meters/second. In some embodiments, a flow rate of a flowing liquid is about 0.5 meters/second to about 1 meters/second. Examples of flow rates include: about 0.01 meter/second, about 0.1 meter/second, about 0.2 meter/second, about 0.3 meter/second, about 0.4 meter/second, about 0.5 meter/second, about 0.6 meter/second, about 0.7 meter/second, about 0.8 meter/second, about 0.9 meter/second, or about 1 meter/second. In some embodiments, a propulsion mechanism comprises a paddle wheel or a pump.

Aqueous Liquid

Systems and methods comprise an aqueous liquid described herein, or a use thereof. In some embodiments, an aqueous liquid comprises a flowing liquid. In some embodiments, a flowing liquid comprises a circulating flow. In some embodiments, a flowing liquid comprises a flow rate.

In some embodiments, an aqueous liquid described herein comprises a pH range of about 4 to about 8.5. In some embodiments, an aqueous liquid comprises a pH of about 4, about 4.1, about 4.2, about 4.3, about 4.4, about 4.5, about 4.6, about 4.7, about 4.8, about 4.9, about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.1, about 8.2, about 8.3, about 8.4, or about 8.5. In some embodiments, an aqueous liquid described herein has a pH of less than 4.0. In some embodiments, the aqueous liquid described herein comprises a pH of greater than 8.5. In some embodiments, an aqueous liquid described herein comprises a pH of about 4 to about 8.5, about 5 to about 7, or about 6.4 to about 6.9. In some embodiments, an aqueous liquid described herein comprises a pH of about 5 to about 7.

An aqueous liquid used herein may be any suitable aqueous liquid that supports the growth of aquatic biomass. In some embodiments, an aqueous liquid may be water. In some embodiments, water is not pure water (i.e., free from non-water molecules). In some embodiments, aqueous liquid used herein comprises one or more of abiotic material, biotic material, and combinations thereof. Abiotic materials include any suitable non-living materials that may help support cultivation of aquatic biomass, such as minerals, vitamins, cofactors, and the like. Biotic materials include any suitable organic materials that may help support cultivation of aquatic biomass, such as symbiotic organisms, flora, fauna, and the like.

Processing Unit(s)

Systems and methods described herein comprise one or more processing units or a use thereof. In some embodiments, one or more processing units are communicatively coupled to one or more measurement devices; one or more light intensity sensors; one or more user interfaces; or any combination thereof. As used herein, the term "communicatively coupled" comprises configuration for two or more objects to communicate data, input, and/or output in a wireless or wired fashion. Wireless communication includes: Bluetooth, wireless networks, and the like. Wired communication includes: ethernet, corded connections, and the like.

In some embodiments, one or more processing units comprise configuration to receive communication from one or more measurement devices; one or more light intensity sensors; one or more user interfaces; or any combination thereof. In some embodiments, configuration to receive communication comprises one or more receivers. In some embodiments, received communication comprises data or input. In some embodiments a receiver receives data transmitted from one or more measurement devices. In some embodiments a receiver receives input transmitted from one or more user interface. In some embodiments a receiver receives data and/or input processed from a central processing unit.

In some embodiments, one or more processing units comprise configuration to process data, input, or both from one or more measurement devices; one or more light intensity sensors; one or more user interfaces; or any combination thereof. In some embodiments, configuration to process data, input, and/or output comprises a central processing unit. In some embodiments, a central processing unit processes data, input, output, or any combination thereof, wherein data, input, and/or output is received or to be transmitted. In some embodiments, a central processing unit processes data and/or input received by one or more receivers. In some embodiments, a central processing unit processes data and/or output to be transmitted by one or more transmitter.

In some embodiments, one or more processing units comprise configuration to transmit communication to one or more measurement devices; one or more light intensity sensors; one or more user interfaces; or any combination thereof. In some embodiments, configuration to transmit communication comprises one or more transmitters. In some embodiments, transmitted communication comprises data, input, output, or any combination thereof. In some embodiments, configuration to transmit communication comprises one or more transmitters. In some embodiments, one or more transmitters transmits data, input, and/or output as processed by a central processing unit. In some embodiments, one or more transmitters transmits data and/or output to one or more user interface. In some embodiments, one or more transmitters transmits input to one or more measurement device.

In some embodiments, one or more receivers comprise configuration to receive light intensity data from one or more measurement devices described herein. In some embodiments, one or more receivers comprises configuration to receive light intensity data from one or more light intensity sensors described herein. In some embodiments, one or more receivers comprise configuration to receive input from one or more user interfaces described herein.

In some embodiments, a central processing unit comprises configuration to process light intensity data to calculate an absorption coefficient. In some embodiments, processing light intensity data comprises calculating light intensity differential from light intensity data. In some embodiments, a light intensity differential is a difference between a ratio of light intensity data in a comparator region to light intensity data in a biomass region and a ratio of light intensity data in a comparator region to light intensity data in a flow obstruction region. In some embodiments, light intensity differential provides an absorption coefficient. In some embodiments, an absorption coefficient may be calculated from the use of the equation set forth in EQUATION 1. In some embodiments, a central processing unit comprises configuration to utilize the equation set forth in EQUATION 1.

In some embodiments, a central processing unit comprises configuration to process a calculated absorption coefficient to determine an aquatic biomass measurement value. In some embodiments, processing a calculated absorption coefficient comprises determining the correlation between an aquatic biomass measurement value and an absorption coefficient. In some embodiments, processing a calculated absorption coefficient comprises the use of EQUATION 2. In some embodiments, a central processing unit comprises configuration to utilize the equation set forth in EQUATION 2. In some embodiments, an aquatic biomass measurement value comprises a value for mass, surface area, density, or combinations thereof of the aquatic biomass in the pond.

Configuration to utilize equations described herein and/or to process data, input, output, or combinations thereof, may comprise the use of software code and/or instructions which are stored in one more processing units, optionally within a central processing unit. In some embodiments, one or more processing units further comprise a memory unit. A memory unit may comprise storage capability for data, input, output, equations, software code, and/or instructions in a readable medium for use by one or more processing unit as described herein.

In some embodiments, one or more transmitters comprises configuration to transmit light intensity data to one or more user interfaces described herein. In some embodiments, one or more transmitters comprise configuration to transmit a calculated absorption coefficient to one or more user interfaces described herein. In some embodiments, one or more transmitters comprise configuration to transmit a determined aquatic biomass measurement value to one or more user interfaces described herein. In some embodiments, one or more transmitters comprise configuration to transmit a determined a value for mass of an aquatic biomass. In some embodiments, one or more transmitters comprise configuration to transmit a determined a value for surface area of an aquatic biomass. In some embodiments, one or more transmitters comprise configuration to transmit a determined a value for density of an aquatic biomass.

In some embodiments, one or more transmitters comprise configuration to transmit input to one or more measurement device described herein. In some embodiments, one or more transmitters comprise configuration to transmit input to one or more light sensor. In some embodiments, one or more transmitters transmit input as processed by a central processing unit and/or as received by a receiver from a user interface.

User Interface(s)

Systems and methods described herein comprise one or more user interfaces or a use thereof. In some embodiments, one or more user interfaces are communicatively coupled to one or more measurement devices; one or more light intensity sensors; one or more processing units; or any combination thereof.

In some embodiments, a user interface comprises configuration to display data and/output transmitted by a transmitter as described herein. In some embodiments, configuration to display data and/output comprises one or more of: a screen, a speaker, or combinations thereof. In some embodiments, a user interface displays light intensity data. In some embodiments, a user interface displays a calculated absorption coefficient. In some embodiments, a user interface displays a determined measurement value for an aquatic biomass.

In some embodiments, a user interface comprises any combination of input and/or output devices that allow a user to provide operator inputs to one or more processing units and/or that allow the one or more processing units to provide feedback to the user, such as a keyboard, keypad, touchpad, touchscreen, pointing device, mouse, buttons, knobs, mobile device, audio input device, audio output device, and/or the like.

Aquatic Biomass

Systems, methods, and devices described herein comprise an aquatic biomass or a use thereof. In some embodiments, an aquatic biomass comprises an aquatic photosynthetic organism. In some embodiments, an aquatic biomass comprises a member of the Bacillariophyta, Chlorophyta, Chrysophyta, Euglenophyta, Euglenozoa, Paeophyta, *Porphyra*, Pyrrophyta, Rhodophyta, or Xanthophyta phylum. In some embodiments, an aquatic biomass comprises a member of the Caulerpaceae, Chlorophyta, Chrysophyta, Chrysophyceae, Cryptophyceae, Dinophyceae, Euglenophyceae, Fucaceae, Florideophyceae, Gigartinaceae, Gracilariaceae, Laminariaceae, Lemnaceae, Salviniaceae, Monostromataceae, Phaeophyceae, Ulvaceae, Xanthophyceae, or Algae family. In some embodiments, an aquatic biomass comprises a member of the *Amphora, Ankistrodesmus, Asteromonas, Azolla, Carteria, Chlamydomonas, Chlorella, Chlorococcum, Chlorogonium,* Chlorophyceace, *Chrysosphaera, Dunaliella, Euglena, Fucus, Furcellaria, Gracilaria, Haematococcus, Laminaria, Landoltia, Lemna, Macrocystis, Monoraphidium, Monostroma, Nannochloropsis, Neochloris, Oedogonium, Ochromona, Oscillatoria, Pelagomonas, Phormidium, Pleurococcus, Porphyra, Pyrobotrys, Sargassum, Scenedesmus, Selenastrum, Spirodela, Spirulina, Volvox, Wolffia,* or *Wolffiella* genus. In some embodiments, an aquatic biomass comprises one or more of the following species: *Lemna aequinoctialis, Lemna disperma, Lemna ecuadoriensis, Lemna gibba* (swollen duckweed), *Lemna japonica, Lemna minor, Lemna minuta, Lemna obscura, Lemna paucicostata, Lemna perpusilla, Lemna tenera, Lemna trisulca, Lemna turionifera, Lemna valdiviana, Lemna yungensis, Landoltia punctata, Spirodela polyrhiza, Wolffia arrhiza, Wolffia globosa, Azolla, Azolla caroliniana, Azolla cristata, Azolla filiculoides, Azolla imbricata, Azolla nilotica, Azolla pinnata, Azolla rubra, Ascophyllum nodosum, Botrydium, Caulerpa, Chondrus crispus,* Euglenoids, *Fucus, Fucus crispus, Fucus serratus, Fucus vesiculosus, Furcellaria lumbricalis, Gracilaria parvispora, Gracilaria tikvahiae, Laminaria digitata, Laminaria farlowii, Laminaria hyperborean, Laminaria nigripes, Macrocystis pyrifera, Monostroma kuroshiense, Monostroma latissimum, Monostroma nitidum, Prymnesium parvum, Palmaria palmata, Saccharina latissima, Tribonema, Ulva intestinalis, Vaucheria,* Achnanthes orientalis, Agmenellum spp., *Amphora coffeiformis, Amphora coffeiformis* var. *linea, Amphora coffeiformis* var. *punctata, Amphora coffeiformis* var. *taylori, Amphora coffeiformis* var. *tenis, Amphora delicatissima, Amphora delicatissima* var. *capitata, Amphora* sp., *Anabaena, Ankistrodesmus, Ankistrodesmus falcatus, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella Candida, Chlorella capsulate, Chlorella desiccate, Chlorella ellipsoidea, Chlorella emersonii, Chlorella fusca, Chlorella fusca* var. *vacuolate, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis* aff. *galbana, Isochrysis galbana, Lepocinclis, Micractinium, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephroselmis* sp., *Nitschia communis, Nitzschia alexandrine, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricornutum, Phacus, Phormidium, Platymonas* sp., *Pleurochrysis camerae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tetraedron, Tetraselmis* sp., *Tetraselmis suecica,* and *Thalassiosira weissflogii.* In some embodiments, an aquatic biomass comprises one or more of duckweed, duckweed fern, mosquito fern, water fern, fairy moss, algae, lesser duckweed, minute duckweed, gibbous duckweed, common duckweed, ivy duckweed, least duckweed, Valdivia duckweed, rockweed, gutweed, green algae, golden algae, golden brown algae, golden brown algae and diatoms, fire algae, red algae, yellow-green algae, brown algae, single-cell algae, microalgae, macroalgae, kombu, kelp, sugarkelp, grass kelp, giant kelp, bladder kelp, sea oak, knotted kelp, knotted wrack, sea lettuce, serrated wrack, carrageen, forked seaweed, brown seaweed, dulse, or dulce sol.

In some embodiments, an aquatic biomass used herein comprises one or more organisms described herein. In some embodiments, an aquatic biomass described herein comprises any chlorophyll-containing plant material. In some embodiments, an aquatic biomass used herein comprises an aquatic surface dwelling plant. In some embodiments, an aquatic biomass used herein comprises *Lemna minor.*

In some embodiments, an aquatic biomass described herein comprises a sequence that has at least about 60%, 65%, 70%, 75%, 80%, 85%, 90%, 95%, 99%, or about 100% sequence identity with any one of the sequences as set forth in SEQ ID NOS: 1-2, and 9-10.

Cultivation of Aquatic Biomass

In some embodiments, systems and methods described herein are useful for cultivating an aquatic biomass. In some embodiments, cultivation of an aquatic biomass comprises cultivating an aquatic biomass in an aqueous liquid as contained by a body of liquid as described herein.

In some embodiments, systems and methods described herein are useful for optimizing growth of an aquatic biomass. Such systems and methods comprise the cultivation of an aquatic biomass and further comprise adjusting an inoculation amount and/or harvest amount of said aquatic biomass as based on a measurement of an aquatic biomass described herein. In some embodiments, an inoculation amount comprises an amount of aquatic biomass to be added to an aqueous liquid. In some embodiments, an inoculation amount may be calculated from EQUATION 3. In some embodiments, an inoculation amount comprises an amount of aquatic biomass to be removed from the aqueous liquid. In some embodiments, a harvest amount may be calculated from EQUATION 4. In some embodiments, one or more processing units, and optionally a central processing unit, may comprise configuration to calculate inoculation amount and/or harvest amount.

In some embodiments, systems and methods described herein further comprise the use of a harvesting unit, wherein the harvesting unit comprises configuration to remove an amount of aquatic biomass from an aqueous liquid. In some embodiments, a harvesting unit comprises an obstruction pipe. In some embodiments, an obstruction pipe is a polyvinyl chloride (PVC) pipe. In some embodiments, an obstruction pipe comprises a pipe with a diameter of about 4 inches to about 6 inches. In some embodiments, an obstruction pipe comprises a pipe with a diameter equal to or greater than a thickness of an aquatic biomass. In some embodiments, an obstruction pipe comprises a diameter of about 1 inch to about 2 inches.

In some embodiments, systems and methods described herein further comprise the use of an inoculation unit, wherein the inoculation unit comprises configuration to add an amount of aquatic biomass to an aqueous liquid. In some embodiments, an inoculation unit comprises a net. In some embodiments, a net is a net bag, hoop net, scoop net, tubular net, mesh net, fishing net, drive-in net, or mounted net.

In some embodiments, targeted optimized growth of an aquatic biomass comprises a mat density of less than about 50 g/m$^2$, from about 50 g/m$^2$ to about 3000 g/m$^2$, or more In some embodiments, targeted optimized growth of an aquatic biomass comprises a mat density of about 50 g/m$^2$, about 100 g/m$^2$, about 200 g/m$^2$, about 400 g/m$^2$, about 600 g/m$^2$, about 800 g/m$^2$, about 1000 g/m$^2$, about 1200 g/m$^2$, about 1400 g/m$^2$, about 1600 g/m$^2$, about 1800 g/m$^2$, about 2000 g/m$^2$, about 2200 g/m$^2$, about 2400 g/m$^2$, about 2600 g/m$^2$, about 2800 g/m$^2$, about 3000 g/m$^2$, or more. In some embodiments, targeted optimized growth of an aquatic biomass comprises a mat density of about 750 g/m$^2$ to about 1500 g/m$^2$.

In some embodiments, targeted optimized growth of an aquatic biomass comprises a mat density of less than 200 g/m$^2$, about 200 g/m$^2$ to about 2000 g/m$^2$, or more. In some embodiments, targeted optimized growth of an aquatic biomass comprises a mat density of about 200 g/m$^2$, about 400 g/m$^2$, about 600 g/m$^2$, about 800 g/m$^2$, about 1000 g/m$^2$, about 1200 g/m$^2$, about 1400 g/m$^2$, about 1600 g/m$^2$, about 1800 g/m$^2$, about 2000 g/m$^2$, or more.

In some embodiments, targeted optimized growth of an aquatic biomass comprises a thickness of about 0.1 mm to about 10 mm, or more. In some embodiments, targeted optimized growth of an aquatic biomass comprises a thickness of about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, about 10 mm, or more. In some embodiments, thickness may be median or average thickness.

In some embodiments, targeted optimized growth of an aquatic biomass comprises a growth rate of about 10 g/m$^2$ per day to about 300 g/m$^2$ per day. In some embodiments, targeted optimized growth of an aquatic biomass comprises a growth rate of about 10 g/m$^2$ per day to about 150 g/m$^2$ per day. In some embodiments, targeted optimized growth of an aquatic biomass comprises a growth rate of about 100 g/m$^2$ per day to about 300 g/m$^2$ per day. In some embodiments, targeted optimized growth of an aquatic biomass comprises a growth rate of about 10 g/m$^2$, about 50 g/m$^2$, about 100 g/m$^2$, about 150 g/m$^2$, about 200 g/m$^2$, about 250 g/m$^2$, or about 300 g/m$^2$ per day. In some embodiments, targeted optimized growth of an aquatic biomass comprises a growth rate of less than about 10 g/m$^2$ per day. In some embodiments, targeted optimized growth of an aquatic biomass comprises a growth rate of more than about 300 g/m$^2$ per day.

In some embodiments, optimizing growth of an aquatic biomass comprises adjusting an inoculation or harvest amount of an aquatic biomass based on a calculated mass, surface area, or density of an aquatic biomass. In some embodiments, optimizing growth of an aquatic biomass comprises adjusting a growth rate. In some embodiments, optimizing growth of an aquatic biomass comprises adjusting aqueous liquid turbidity, temperature, pH, nutrients concentration, flow rate, light intensity, and the like.

In some embodiments, systems and methods for measuring aquatic biomass described herein are useful for maximizing plant protein harvest. Such systems and methods comprise the cultivation of an aquatic biomass, optimizing growth of an aquatic biomass, and further comprise harvesting aquatic biomass for use the production of plant protein, wherein said plant protein harvested is thereby maximized. In some embodiments, upon harvesting plant protein, systems and methods described herein further comprise a system of or a method of plant protein production.

Plant Protein Production and Isolation

In some embodiments, systems and methods described herein are useful for the production of plant protein. In some embodiments, methods of plant production comprise: measuring an aquatic biomass measurement as described herein, harvesting aquatic biomass upon reaching the targeted biomass measurement, and extracting plant protein from the harvested aquatic biomass. In some embodiments, provided herein are compositions comprising plant protein described herein.

Proteins can be extracted from aquatic biomass through any known processes, wherein aquatic biomass generally comprises plant material. For example, plant material containing protein, such as RuBisCO, can be homogenized and the protein extracted from the pulp and/or liquid. The extract can be further clarified, filtered, and washed to arrive at the described protein isolate. Other extraction processes can include solvent extraction (e.g., using polar solvents, organic solvents, or supercritical fluids), chromatography (e.g., preparative liquid chromatography), clarification, distillation, filtration (e.g., ultrafiltration), recrystallization, and/or solvent-solvent partitioning.

In some embodiments, described herein is a process for making a purified protein isolate from a plant material, comprising the steps of: a) providing the plant material in a solution comprising a reducing agent; b) lysing the plant material; c) separating the lysed plant material into a solid phase and a liquid phase, wherein the liquid phase contains soluble protein and chlorophyll; d) coagulating the chlorophyll in the liquid phase by heating it to a first set temperature in no more than about 30 min, then cooling it to a second set temperature in no more than about 30 min, wherein the cooling is initiated when the liquid phase reaches the first set temperature; e) contacting the liquid phase of d) with a flocculant and/or an adsorbent, and mixing for a period of time sufficient to flocculate and/or adsorb chlorophyll in the liquid phase to the adsorbent, thereby forming a flocculated mixture; f) separating the flocculated mixture of e) into a solid phase and a liquid phase; and g) filtering the liquid phase of f) to yield a filtrate containing a purified protein. In some embodiments, the plant material is harvested and cleaned before the process is started. For instance, in some embodiments, the plant material is chemically washed or washed with water prior to processing. In some embodiments, the plant material is washed more than one time prior to processing.

In some embodiments, the plant material is mixed in a solution comprising a reducing agent. Examples of reducing agents suitable for use in the disclosed processes include, but are not limited to, 2-mercaptoethanol (BME), 2-mercaptoethylamine-HCL, sodium sulfite, magnesium sulfite, sodium metabisulfite, sodium bisulfite, cysteine hydrochloride, dithiothreitol (DTT), glutathione, cysteine, tris(2-carboxyethyl) phosphine (TCEP), ferrous ion, nascent hydrogen, sodium amalgam, oxalic acid, formic acid, magnesium, manganese, phosphorous acid, potassium, sodium, and any combination thereof. Said solution may comprise other components to provide beneficial properties to the solution or to the process. Examples such components include buffering agents, chelating agents, protease inhibitors, pH adjustors, and the like.

Lysing can be through any suitable method to disrupt plant material and release cellular contents, such as a plant cell's cytoplasm. Types of lysing described herein include mechanical, chemical, and/or enzymatic lysis. Mechanical lysing encompassed by the processes described herein includes, but is not limited to, mechanical agitation, pressure, grinding, squeezing, shearing, using a blender, using a mill, using a press, a sonicator, a nitrogen burst, ultrasonic energy, by freezing, using a homogenizer, a pulse electric field, a disintegrator, more than one of the foregoing, or any combination thereof. Chemically lysing encompassed by the processes described herein includes, but is not limited to, lysed chemically using one or more of detergents (e.g., ionic, cationic, anionic, sodium dodecyl sulfates, non-ionic, zwitterionic, hypotonic, hypertonic, and isotonic detergents and the like). Chemically lysing encompassed by the processes described herein includes, but is not limited to, using one or more enzymes, such as cellulase and/or pectinase. Separation of the lysed plant material and/or flocculated mixture into solid phase and a liquid phase may be performed by any suitable solid-liquid separation technique. Suitable solid-liquid separation techniques include but are not limited to: gravity settling, sieving (e.g., circular vibratory separator or a linear/inclined motion shaker), filtration (e.g., dead-end filtration system, using ultrafiltration, using a tangential flow filtration system, or using a plate filter), centrifugation (e.g., disk stack centrifuge, a decanter centrifuge, a continuous centrifuge, or a basket centrifuge), a press (e.g., screw press, a French press, a belt press, a filter press, a fan press, a finisher press, or a rotary press), or decanting (e.g., using a decantor), or any combination thereof.

The process for making the protein isolates described herein can also comprise a step of coagulating components that are undesired (e.g., components that are not protein, such as RuBisCO) using any suitable method to effect coagulation. Examples include, but are not limited to: heat treatment, cooling; addition of one or more salts (e.g., a calcium salt, a magnesium salt, a beryllium salt, a zinc salt, a cadmium salt, a copper salt, an iron salt, a cobalt salt, a tin salt, a strontium salt, a barium salt, a radium salt, calcium chloride, calcium nitrate, or iron carbonate potassium phosphate, calcium chloride, or any combination thereof); addition of quaternary ammonia specie; addition of a polymer based coagulate; electrocoagulation; and the like.

The process for making the protein preparation may also comprise a step of contacting the liquid phase with a flocculant and/or an adsorbent and mixing for a period of time sufficient to flocculate and/or adsorb chlorophyll in the liquid phase to the adsorbent, thereby forming a flocculated mixture. Any suitable process of flocculation can be used and exemplary flocculants may include, but are not limited to, an alkylamine epichlorohydrin, polydimethyldiallylammonium chloride, a polysaccharide (e.g., chitosan), a polyamine, starch, aluminum sulphate, alum, polyacrylamide, polyacromide, or polyethyleneimine. Any suitable adsorbent can be used and exemplary adsorbents may include activated carbon, graphite, silica gel, zeolites, clay, polyethylene, and resins (e.g., ion-exchange resins, size exclusion chromatography (SEC) resins, affinity based resins, or hydrophobicity based resin).

After the separation of the flocculated mixture into a solid phase and a liquid phase, the liquid phase may be filtered to yield a filtrate containing the purified protein. Any suitable method of filtration can be used and include, for example, the use of surface filters, depth filters, by membrane filtration, column filtration, diafiltration, ultrafiltration, tangential flow filtration, filtration with diatomaceous earth, filtration with silt, filtration with activated carbon, and the like.

Liquid phases and/or filtrates can be further sterilized, concentrated, dialyzed, dried, and/or otherwise processed to provide protein isolates for use herein. In some embodiments, liquid phases and/or filtrates may be dried. In some embodiments, drying may be accomplished using a spray dryer, a freeze dryer, drum drying, film drying, bed drying, a flash dryer, or a rotary dryer.

In some embodiments, the purity of protein isolates described herein is at least about 30%, 40%, 50%, 60%, 70%, 80%, 90%, 95%, or more. In some embodiments, the purity of protein isolate described herein is 80% or more. In certain embodiments, protein isolates described herein may contain no more than 50%, 40%, 30%, 20% 10% or less impurities. In certain embodiments, protein isolates described herein may contain no more than 20% 10% or less impurities. In some embodiments, processes described herein produce one or more by-products, such as sodium hydroxide.

In some embodiments, the methods of plant protein production described herein comprise extracting plant protein isolate from harvest aquatic biomass. In some embodiments, plant protein isolate is RuBisCO, wheat gluten, a dehydrin protein, an albumin, a conglycinin, a globulin, a zein, a leghemoglobin, a non-symbiotic hemoglobin, or a cytoplasmic actin. Non-limiting examples of suitable plant proteins include RuBisCO, an algal protein, a seaweed protein, an albumin, a gluten, a glycinin, a conglycinin, a legumin, a globulin, a vicilin, a conalbumin, a gliadin, a glutelin, a glutenin, a hordein, a prolamin, a phaseolin, a proteinoplast, a secalin, a triticeae gluten, a zein, an oleosin, a caloleosin, a steroleosin, or mixtures thereof (e.g., albumin fractions). In some embodiments, plant protein isolate is RuBisCo.

In some embodiments, plant protein isolate described herein can be used to formulate compositions for use herein. In some embodiments, RuBisCO used in compositions disclosed herein is isolated from one or more sources described herein.

In some embodiments, a RuBisCO protein isolate is free from other substances, including naturally occurring substances, such as chlorophyll, and/or substances added to isolate RuBisCO protein from a RuBisCO source, such as a solvent or water. In some embodiments, RuBisCO protein isolate is chlorophyll-free. In some embodiments, RuBisCO is also flavorless, tasteless, colorless, and/or uncolored.

Subsequent extraction, RuBisCO proteins may be further processed to improve the purity of the protein sample. In other scenarios, the extracted RuBisCO may undergo further processing (e.g., adjusting the pH, adjusting the heat, etc.) in order to concentrate the extracted proteins.

Additionally, extracted RuBisCO proteins may also be combined with other proteins, where such combination may occur before or after the additional processing described. In some embodiments, RuBisCO protein isolate comprises other proteins, including but not limited to: pea proteins, isolates, and/or concentrates; garbanzo (chickpea) proteins, isolates, and/or concentrates; fava bean proteins, isolates, and/or concentrates; soy proteins, isolates, and/or concentrates; rice proteins, isolates, and/or concentrate; potato proteins, isolates, and/or concentrates; hemp proteins, isolates, and/or concentrates; canola proteins, isolates, and/or concentrates; wheat proteins, isolates, and/or concentrates; corn proteins, isolates, and/or concentrates; zein proteins, isolates, and/or concentrates; rice proteins, isolates, and/or concentrates; oat proteins, isolates, and/or concentrates; potatoes proteins, isolates, and/or concentrates; peanut proteins, isolates, and/or concentrates; legumes/pulses proteins, isolates, and/or concentrates; lentils proteins, isolates, and/or concentrates; or any combinations thereof. RuBisCO protein and other protein combinations. In some examples, RuBisCO and additional proteins may be in a dry form (e.g., powdered, pelletized, or the like). In other examples, the RuBisCO and the additional proteins may be in a liquid form or in a liquid solution. In some embodiments, a RuBisCO protein isolate from one source, may be combined with a RuBisCO protein isolate from separate source. For example, RuBisCO protein isolate may be extracted from an aquatic biomass (e.g., *Lemna minor*) and combined with RuBisCO extracted from a second source (e.g., *Chlorella vulgaris*).

In some embodiments, the RuBisCO protein isolate comprises protein comprising a sequence that has at least about 60%, 65%, 70%, 75%, 80%, 85%, 90%, 95%, 99%, or about 100% sequence identity with any one of the sequences as set forth in TABLE 1. In some embodiments, the RuBisCO protein isolate comprises protein comprising a sequence that has at least about 60%, 65%, 70%, 75%, 80%, 85%, 90%, 95%, 99%, or about 100% sequence identity with more than one of the sequences as set forth in TABLE 1. In some embodiments, the RuBisCO protein isolate comprises one or more protein comprising one or more sequences, each of which has at least about 60%, 65%, 70%, 75%, 80%, 85%, 90%, 95%, 99%, or about 100% sequence identity with any one of the sequences as set forth in SEQ ID NOs: 1 to 10. Provided in TABLE 1 are large and small RuBisCO subunits for various species described herein, including *Lemna minor, Nicotiana tabacum, Medicago sativa* (alfalfa), *Spinacia oleracea* (Spinach), and *Chlorella vulgaris* (green algae).

TABLE 1

RUBISCO SEQUENCES

| SEQ ID NO: | Sequence |
|---|---|
| 1 | MSPQTETKASAGFKAGVKDYKLNYYTPEYETKDTDILAAFRVTP QPGVPPEEAGAAVAAESSTGTWTTVWTDGLTSLDRYKGRCYHIE PVAGEENQFIAYIAYPLDLFEEGSVTNMFTSIVGNVFGFKALRA LRLEDLRIPPAYSKTFQGPPHGIQVERDKLNKYGRPLLGCTIKP KLGLSAKNYGRAVYECLRGGLDFTKDDENVNSQPFMRWRDRFLF CAEAIYKAQAETGEIKGHYLNATAGTCEEMIKRAVFARELGVPI VMHDYLTGGFTANTSLAYYCRDNGLLLHIHRAMHAVIDRQKNHG MHFRVLAKALRMSGGDHVHSGTVVGKLEGEREMTLGFVDLLRDD FIEKDRSRGIFFTQDWVSMPGVLPVASGGIHVWHMPALTEIFGD DSVLQFGGGTLGHPWGNAPGAVANRVALEACVKARNEGRDLARE GNEIIREACNWSPELAAACEVWKEIKF EYEPVDKLDVK |
| 2 | MASSMMASTAAAVARAGPAQSSMVPFNACRSSVPFPATRKANNN LSTLPGNGGRVSCMQVWPPEGLKKFETLSYLPPLSVEDLAKEVD YLLRNDWVPCIEFSKEGFVYRENHASPGYYDGRYWTMWKLPMFG CTDASQVIAEVEEAKKAYPEYFVRIIGFDNKRQVQCISFIAYKP T |
| 3 | MSPQTETKASVGFKAGVKEYKLTYYTPEYQTKDTDILAAFRVTP QPGVPPEEAGAAVAAESSTGTWTTVWTDGLTSLDRYKGRCYRIE RVVGEKDQYIAYVAYPLDLFEEGSVTNMFTSIVGNVFGFKALRA LRLEDLRIPPAYVKTFQGPPHGIQVERDKLNKYGRPLLGCTIKP KLGLSAKNYGRAVYECLRGGLDFTKDDENVNSQPFMRWRDRFLF CAEAIYKAQAETGEIKGHYLNATAGTCEEMIKRAVFARELGVPI VMHDYLTGGFTANTSLAHYCRDNGLLLHIHRAMHAVIDRQKNHG IHFRVLAKALRMSGGDHIHSGTVVGKLEGERDITLGFVDLLRDD FVEQDRSRGIYFTQDWVSLPGVLPVASGGIHVWHMPALTEIFGD DSVLQFGGGTLGHPWGNAPGAVANRVALEACVKARNEGRDLAQE GNEIIREACKWSPELAAACEVWKEIVFNFAAVDVLDK |
| 4 | MAFLIMSSAAAVATGTNAAQASMIAPFTGLKSATSFPVSRKQNL DITSIASNGGRVQCMQVWPPINKKKYETLSYLPDLSEEQLLREV EYLLKNGWVPCLEFETEHGFVYRENNKSPGYYDGRYWTMWKLPM FGCTDATQVLAEVEEAKKAYPQAWIRIIGFDNVRQVQCISFIAY KPEGY |
| 5 | MSPQTETKATVGFKAGVKDYRLTYYTPDYETKDTDILAAFRVSP QPGVPAEEAGAAVAAESSTGTWTTVWTDGLTSLDRYKGRCYHIE PVAGEETQFIAYVAYPLDLFEEGSVNYMFTSIVGNVFGFKALRA LRLEDLRIPAAYVKTFQGPPQGIQVERDKLNKYGRPLLGCTIKP KLGLSAKNYGRAVYECLRGGLDFTKDDENVNSQPFMRWRDRFLF CAEAIYKAQAETGEIKGHYLNATAGTCEEMMKRAVFARELGVPI VMHDYLTVGFTANTTLAHYCRDNGLLLHIHRAMHAVIDRQKNHG MHFRVLAKALRMSGGDHIHAGTVVGKLEGERDITLGFVDLLRDD FIEKDRSRGIFFTQDWVSLPGVLPVASGGIHVWHMPALTEIFGD DSVLQFGGGTLGHPWGNAPGAVANRVALEACVQARNEGRDTLAR EGNEIIREAKWSPELAAACEVWKEIKFEFPAMDN |
| 6 | MALISSAAVTTVNRASSAQANLVAPFTGLKSSAGFPVTKKTNND ITSIASNGGRVNCMQVWPPVGKKKFETLSYLPPLTEEQLAKEVE YLIRKGWIPCLEFELEKGFVYRENHRSPGYYDGRYWTMWRLPLF GATDSSQVLKELADCKAEYPDSFIRIIGFDNVRQVQCISFIAHT PKNY |
| 7 | MSPQTETKASVEFKAGVKDYKLTYYTPEYETLDTDILAAFRVSP QPGVPPEEAGAAVAAESSTGTWTTVWTDGLTNLDRYKGRCYHIE PVAGEENQYICYVAYPLDLFEEGSVTNMFTSIVGNVFGFKALRA LRLEDLRIPVAYVKTFQGPPHGIQVERDKLNKYGRPLLGCTIKP KLGLSAKNYGRAVYECLRGGLDFTKDDENVNSQPFMRWRDRFLF CAEALYKAQAETGEIKGHYLNATAGTCEDMMKRAVFARELGVPI VMHDYLTGGFTANTTLSHYCRDNGLLLHIHRAMHAVIDRQKNHG MHFRVLAKALRLSGGDHIHSGTVVGKLEGERDITLGFVDLLRDD |

TABLE 1-continued

RUBISCO SEQUENCES

| SEQ ID NO: | Sequence |
|---|---|
| | YTEKDRSRGIYFTQSWVSTPGVLPVASGGIHVWHMPALTEIFGD DSVLQFGGGTLGHPWGNAPGAVANRVALEACVQARNEGRDLARE GNTIIREATKWSPELAAACEVWKEIKFEFPAMDTV |
| 8 | MQVWPPLGLKKFETLSYLPPLTTEQLLAEVNYLLVKGWIPPLEF EVKDGFVYREHDKSPGYYDGRYWTMWKLPMFGGTDPAQVVNEVE EVKKAPPDAFVRFIGFNDKREVQCISFIAYKPAGY |
| 9 | MSPQTETKARVGFKAGVKDYRLTYYTPDYQPKDTDILAAFRMTP QPGVPPEEAGAAVAAESSTGTWTTVWTDGLTSLDRYKGRCYDIE PVPGEENQYIAYIAYPLDLFEEGSVTNLFTSIVGNVFGFKALRA LRLEDLRIPPAYVKTFQGPPHGIQVERDKLNKYGRGLLGCTIKP KLGLSAKNYGRAVYECLRGGLDFTKDDENVNSQPFMRWRDRFLF VAEAIYKSQAETGEIKGHYLNATAATAEAMMQRAECAKDLGVPI IMHDYLTGGFTANTSLSHYCRDNGLLLHIHRAMHAVIDRQRNHG ITFRVLAKALRLSGGDHLHSGTVVGKLEGEREVTLGFVDLMRDD YIEKDRSRGIYFTQDWVSLPGTMPVASGGIHVWHMPALVEIFGD DACLQFGGGTLGHPWGNAPGAAANRVALEACTQARNEGRDLARE GGDVIRAACKWSPELAAACEVWKEIKFEFETIDTL |
| 10 | MAALTASLVSCPVAVAAKPARLASPAWPASLSPRRLSPPSPRGP SQTAAAPARCSCGSPLTTSSSRPSPTCPSDRRPDRQAGRLHHPS GWTPALEFSNAESAYVKDVANIRFTGGSASCNYYDNRYWAMYKL PMFGCTDASQVLAEIANAVKTFPDSYVRMAAFDAVRQVQTVAIL VHRPASATDYRLPENPQPLIGCTTQLERPQYCKSLANL |

In some embodiments, a RuBisCO protein isolate comprises protein comprising sequence that has at least 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO: 1 or 2 or both.

In some embodiments, a RuBisCO protein isolate comprises protein comprising sequence that has at least 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO: 3 or 4 or both.

In some embodiments, a RuBisCO protein isolate comprises protein comprising sequence that has at least 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO: 5 or 6 or both.

In some embodiments, a RuBisCO protein isolate comprises protein comprising sequence that has at least 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO: 7 or 8 or both.

In some embodiments, a RuBisCO protein isolate comprises protein comprising sequence that has at least 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO: 9 or 10 or both.

RuBisCO is composed of 8 large subunits with a molecular mass of about 53 kDalton and 8 small subunits with a molecular mass of about 12 kDalton. Accordingly, in some embodiments, a disclosed RuBisCO protein isolate comprises one or more large subunits, one or more small subunits, or any combination thereof. For example, a RuBisCO protein isolate includes a large subunit, a small subunit or both. In some embodiments, a RuBisCO subunit comprises an amino acid sequence in any one of the Uniprot records set forth in TABLE 2.

TABLE 2

RUBISCO SUBUNITS

| Subunit | Uniprot Accession Number |
|---|---|
| Large | A9L9A4, A0A3GlN0S3, K4Fl51, A0A3GlMVZ6, H9ALP2, D6NJG9, Q8WHI2, G8D4W8, D3W4G8, H9ALP3, G0WYT7, B5WX54, A0A1S7JIB4, A0A482K3Y6, R9S086, A0A411PP11, D6NJG2, H9AHZ6, Q8WHI1, R4I7N5, O85040, Q31NB3, P00880, P00875, P00879, O93627, O03042, P0C2C2, P04718, P00877, P0C512, P04717, P00876, Pll383, P22849, Q8DIS5, P22859, O85040,B0Z5Bl, Q31HD8, P22850, |
| Small | P19309, P19308, P19310, P19311, Pl9312, P00872, P10795, B3H5S2, P10796, P10797, A0A0S4IJL0, P45686, P04716, P69249, Q0INY7, Q31NB2, P05348, P08475, P00873, |

In some embodiments, a RuBisCO protein isolate comprises protein comprising sequence that has at least 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to an amino acid sequence as set forth in any one of the records described in TABLE 2.

In some embodiments, a disclosed RuBisCO protein isolate comprises protein comprising about 4 to about 478 contiguous amino acids, but is less than the full-length, native or naturally occurring, wild-type ribulose-1,5-bisphosphate carboxylase/oxygenase polypeptide. In some embodiments, a disclosed RuBisCO protein isolate comprises protein comprising about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, about 140, about 141, about 142, about 143, about 144, about 145, about 146, about 147, about 148, about 149, about 150, about 151, about 152, about 153, about 154, about 155, about 156, about 157, about 158, about 159, about 160, about 161, about 162, about 163, about 164, about 165, about 166, about 167, about 168, about 169, about 170, about 171, about 172, about 173, about 174, about 175, about 176, about 177, about 178, about 179, about 180, about 181, about 182, about 183, about 184, about 185, about 186, about 187, about 188, about 189, about 190, about 191, about 192, about 193, about 194, about 195, about 196, about 197, about 198, about 199, about 200, about 201, about 202, about 203, about 204, about 205, about 206, about 207, about 208, about 209, about 210, about 211, about 212, about 213, about 214, about 215, about 216, about 217, about 218, about 219, about 220, about 221, about 222, about 223, about 224, about 225, about 226, about 227, about 228, about 229, about 230, about 231, about 232, about 233, about 234, about 235, about 236, about 237, about 238, about 239, about 240, about 241, about 242, about 243, about 244, about 245, about 246, about 247, about 248, about 249, about 250, about 251, about 252, about 253, about 254, about 255, about 256, about 257, about 258, about 259, about 260, about 261, about 262, about 263, about 264, about 265, about 266, about 267, about 268, about 269, about 270, about 271, about 272, about 273, about 274, about 275, about 276, about 277, about 278, about 279, about 280, about 281, about 282, about 283, about 284, about 285, about 286, about 287, about 288, about 289, about 290, about 291, about 292, about 293, about 294, about 295, about 296, about 297, about 298, about 299, about 300, about 301, about 302, about 303, about 304, about 305, about 306, about 307, about 308, about 309, about 310, about 311, about 312, about 313, about 314, about 315, about 316, about 317, about 318, about 319, about 320, about 321, about 322, about 323, about 324, about 325, about 326, about 327, about 328, about 329, about 330, about 331, about 332, about 333, about 334, about 335, about 336, about 337, about 338, about 339, about 340, about 341, about 342, about 343, about 344, about 345, about 346, about 347, about 348, about 349, about 350, about 351, about 352, about 353, about 354, about 355, about 356, about 357, about 358, about 359, about 360, about 361, about 362, about 363, about 364, about 365, about 366, about 367, about 368, about 369, about 370, about 371, about 372, about 373, about 374, about 375, about 376, about 377, about 378, about 379, about 380, about 381, about 382, about 383, about 384, about 385, about 386, about 387, about 388, about 389, about 390, about 391, about 392, about 393, about 394, about 395, about 396, about 397, about 398, about 399, about 400, about 401, about 402, about 403, about 404, about 405, about 406, about 407, about 408, about 409, about 410, about 411, about 412, about 413, about 414, about 415, about 416, about 417, about 418, about 419, about 420, about 421, about 422, about 423, about 424, about 425, about 426, about 427, about 428, about 429, about 430, about 431, about 432, about 433, about 434, about 435, about 436, about 437, about 438, about 439, about 440, about 441, about 442, about 443, about 444, about 445, about 446, about 447, about 448, about 449, about 450, about 451, about 452, about 453, about 454, about 455, about 456, about 457, about 458, about 459, about 460, about 461, about 462, about 463, about 464, about 465, about 466, about 467, about 468, about 469, about 470, about 471, about 472, about 473, about 474, about 475, about 476, about 477, or about 478 contiguous amino acids of SEQ ID NO: 1, 2, both, one or more large subunits set forth in TABLE 2, one or more small subunits set forth in TABLE 2, or any combination thereof, but is less than the full-length, native or naturally occurring, wild-type ribulose-1,5-bisphosphate carboxylase/oxygenase polypeptide.

In some embodiments, compositions disclosed herein comprise about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% protein isolate by dry weight or total weight. In some embodiments, the compositions comprise about 5% to about 80%, about 6% to about 50%, about 7% to about 40%, about 8% to about 30%, about 9% to about 20%, or about 10% to about 15% protein isolate by dry weight or total weight. In certain embodiments, total weight includes a preservative solution. In some embodiments, description of a measurement by weight is understood to encompass dry weight or total weight.

In some embodiments, compositions disclosed herein comprise about 1 g to about 100 g of protein isolate. In some embodiments, compositions disclosed herein comprise about 1 g, about 2 g, about 3 g, about 4 g, about 5 g, about 6 g, about 7 g, about 8 g, about 9 g, about 10 g, about 20 g, about 30 g, about 40 g, about 50 g, about 60 g, about 70 g, about 80 g, about 90 g, about 100 g, or more of a protein isolate, such as a RuBisCO protein isolate.

Measurement Device(s)

Provided herein are one or more measurement devices for measuring an aquatic biomass. In some embodiments, devices for measuring comprises: a shield and one or more light intensity sensors to collect one or more measurements of light intensity as described herein. In some embodiments, a measurement device further comprises one or more arms.

In some embodiments, one or more measurement devices comprises a shield. In some embodiments, a shield obstructs at least a portion of an aquatic biomass in an area adjacent to a shield, creating a flow obstruction region. In some embodiments, a flow obstruction region is an area substantially free of aquatic biomass. In some embodiments, a shield obstructs at least a portion of an aquatic biomass from contacting one or more light intensity sensor.

In some embodiments, a shield comprises at least one wall. In some embodiments, a shield comprises at least one wall wherein the at least one wall bisects an aqueous liquid and/or at least a portion of an aquatic biomass. In some embodiments, at least one wall bisects an aqueous liquid and/or at least a portion of an aquatic biomass so that at least a portion of an aquatic biomass is dispersed from contacting a flow obstruction region.

In some embodiments, a shield comprises at least one wall wherein the at least one wall is curved, optionally u-shaped. In some embodiments, a shield comprises at least one wall wherein the at least one wall is straight. In some embodiments, a shield comprises at least one wall wherein the at least one wall extends laterally. In some embodiments, a shield comprises at least one wall, at least two walls, at least three walls, at least four walls, or more. In some embodiments, wherein the shield comprises more than one wall wherein said walls are contiguously connected to one another. In some embodiments, a shield comprises more than one wall, wherein said walls are affixed along a longitudinal axis. In some embodiments, the at least one wall comprises metal, plastic polymer, copper, galvanized iron, polyvinyl chloride (PVC), or combinations thereof.

In some embodiments, a shield comprises a base. In some embodiments, a shield comprises a base contiguously connected to at least one wall. In some embodiments, a shield comprises a base, wherein the base is affixed to at last one wall along a lateral axis. In some embodiments, the base comprises metal, plastic polymer, copper, galvanized iron, polyvinyl chloride (PVC), or combinations thereof.

In some embodiments, a shield comprises a vent. In some embodiments, a shield comprises a vent affixed into at least one wall. In some embodiments, a shield comprises a frame. In some embodiments, a shield comprises a frame configured to support one or more of: at least one wall, a base, one or more arms, one or more light intensity sensors, or combinations thereof. In some embodiments, the frame comprises metal, plastic polymer, copper, galvanized iron, polyvinyl chloride (PVC), or combinations thereof.

In some embodiments, one or more measurement devices comprises one or more arms. In some embodiments, one or more arms comprises configuration to support one or more light intensity sensors. In some embodiments, one or more measurement devices comprises one or more, two or more, or three or more arms. In some embodiments, the measurement device comprises more than one arm wherein each arm comprises configuration to support one or more light intensity sensors. In some embodiments, the one or more arms comprises metal, plastic polymer, copper, galvanized iron, polyvinyl chloride (PVC), or combinations thereof.

In some embodiments, a measurement device described herein comprises one or more light intensity sensors. In some embodiments, a measurement device described herein comprises one or more, two or more, three or more light intensity sensors. In some embodiments, the one or more light intensity sensors are one or more optical sensors. In some embodiments, the one or more optical sensors measure light intensity across a range of exposure levels, such as full sunlight, partial sunlight, partial shade, full shade, and partial darkness. In some embodiments, the device comprises a light source. In some embodiments, the one or more optical sensors are one or more light meters, one or more lux meters, one or more UV meter, one or more photosynthetically active radiation (PAR) sensor, one or more camera, or combinations thereof. In some embodiments, the one or more optical sensors measure photometric units. In some embodiments, the one or more optical sensors measure lumens per unit area. In some embodiments, the one or more optical sensors measure lux or lumens per square meter. In some embodiments, the one or more optical sensors comprise one or more lux meters. In some embodiments, the one or more optical sensors comprise one or more light meters. In some embodiments, the one or more optical sensors comprise one or more cameras. In some embodiments, the one or more cameras are a digital camera, non-digital camera, integrated camera, single camera, dual camera, timer-specific camera, or combinations thereof. In some embodiments, the one or more cameras have a depth of at least 8 bits per pixel. In some embodiments, the one or more cameras have a depth of about 8 bits to about 16 bits per pixel. In some embodiments, the one or more cameras have a depth of about 8 bits to about 12 bits per pixel. In some embodiments, the one or more cameras have a depth of about 10 bits to about 14 bits per pixel. In some embodiments, the one or more cameras have a depth of about 12 bits to about 16 bits per pixel. In some embodiments, the one or more cameras have a depth of about 8 bits, about 10 bits, about 12 bits, about 14 bits, or about 16 bits. In some embodiments, the one or more cameras have a depth of more than about 16 bits per pixel.

In some embodiments, the one or more optical sensors measure photometric units over a time interval. In some embodiments, the one or more optical sensors measure photometric units once over a time interval of about 30 seconds to about 10 minutes. In some embodiments, the one or more optical sensors measure photometric units once over a time interval of about 30 seconds to about 2 minutes. In some embodiments, the one or more optical sensors measure photometric units once over a time interval of about 1 minute to about 5 minutes. In some embodiments, the one or more optical sensors measure photometric units once over a time interval of about 4 minutes to about 10 minutes. In some embodiments, the one or more optical sensors measure photometric units once over a time interval of about 30 seconds, about 1 minute, about 3 minutes, about 5 minutes, about 7 minutes, about 9 minutes, or about 10 minutes. In some embodiments, the one or more optical sensors measure photometric units once over a time interval of less than about 30 seconds. In some embodiments, the one or more optical sensors measure photometric units once over a time interval of more than about 10 minutes. In some embodiments, the one or more optical sensors measure lumens per square meter from about 0 lux to about 75,000 lux. In some embodiments, the one or more optical sensors measure lumens per square meter from about 0 lux to about 30,000 lux. In some embodiments, the one or more optical sensors measure lumens per square meter from about 25,000 lux to about 50,000 lux. In some embodiments, the one or more optical sensors measure lumens per square meter from about 45,000 lux to about 75,000 lux. In some embodiments, the one or more optical sensors measure lumens per square meter of about 0 lux, about 10,000 lux, about 20,000 lux, about 25,000 lux, about 30,000 lux, about 40,000 lux, about 50,000 lux, about 60,000 lux, about 70,000 lux, about 75,000 lux. In some embodiments, the one or more optical sensors measure lumens per square meter of more than about 75,000 lux.

In some embodiments, the one or more optical sensors measure lumens per square meter at a temperature of about 1° C. to about 45° C. In some embodiments, the one or more optical sensors measure lumens per square meter at a temperature of about 1° ° C. to about 11° C. In some embodiments, the one or more optical sensors measure lumens per square meter at a temperature of about 10° ° C. to about 40° C. In some embodiments, the one or more optical sensors measure lumens per square meter at a temperature of about 30° C. to about 45° C. In some embodiments, the one or more optical sensors measure lumens per square meter at a temperature of about 0° C., about 5° C., about 10° C., about 15° C., about 20° C., about 25° C., about 30° C., about 35° C., about 40° C., about 45° C. In some embodiments, the one or more optical sensors measure lumens per square meter at a temperature of less than about 1° C. In some embodiments, the one or more optical sensors measure lumens per square meter at a temperature of more than about 45° C.

In some embodiments, the one or more optical sensors comprise one or more PAR sensor. In some embodiments, the one or more PAR sensor measures light absorption at 400 nanometers to 700 nanometers wavelength. In some embodiments, the one or more PAR sensor measures light absorption at about 400 nanometers, about 500 nanometers, or about 700 nanometers. In some embodiments, the one or more PAR sensor measures light absorption at less than about 400 nanometers wavelength. In some embodiments, the one or more PAR sensor measures light absorption at more than about 700 nanometers wavelength.

In some embodiments, the one or more optical sensors comprise one or more light intensity sensor. In some embodiments, the one or more light intensity sensor measures light absorption at 10 nanometers to 400 nanometers wavelength. In some embodiments, the one or more light intensity sensor measures light absorption at 400 nanometers to 700 nanometers wavelength. In some embodiments, the one or more light intensity sensor measures light absorption at 750 nanometers to 10,000 nanometers wavelength. In some embodiments, the one or more light intensity sensor measures light absorption at 10 nanometers to 500 nanometers wavelength. In some embodiments, the one or more light intensity sensor measures light absorption at 400 nanometers to 750 nanometers wavelength. In some embodiments, the one or more light intensity sensor measures light absorption at 700 nanometers to 10,000 nanometers wavelength. In some embodiments, the one or more light intensity sensor measures light absorption at about 10 nanometers, about 250 nanometers, about 400 nanometers, about 500 nanometers, about 700 nanometers, about 750 nanometers, about 1,000 nanometers, about 2,000 nanometers, about 3,000 nanometers, about 4,000 nanometers, about 5,000 nanometers, about 6,000 nanometers, about 7,000 nanometers, about 8,000 nanometers, about 9,000 nanometers, or about 10,000 nanometers. In some embodiments, the one or more light intensity sensor measures light absorption at more than about 10,000 nanometers wavelength.

In some embodiments, a light intensity sensor collects light intensity data in the region of which the light intensity sensor is placed. In some embodiments, one or more light intensity sensors is positioned to collect light intensity data from a comparator region. In some embodiments, one or more light intensity sensors is positioned to collect light intensity data from a biomass region. In some embodiments, one or more light intensity sensors is positioned to collect light intensity data from a flow obstruction region. In some embodiments wherein more than one light intensity sensor is used, and each of the more than one light intensity sensor collects light intensity data from the same region, it is said that a set of light intensity sensors are used. In some embodiments wherein two light intensity sensors are used, each light intensity sensor may collect light intensity data from a comparator region, a biomass region, a flow obstruction region, or combinations thereof. In some embodiments wherein three light intensity sensors are used, each light intensity sensor may collect light intensity data from a comparator region, a biomass region, or a flow obstruction region. In some embodiments, three or more light intensity sensors are used, wherein each light intensity sensor may collect light intensity data from a comparator region, a biomass region, or a flow obstruction region.

In some embodiments, the one or more light intensity sensors comprise configuration to communicate data measurements. In some embodiments, the one or more light intensity sensors comprise configuration to communicate data measurements to one or more processing units as described herein.

In some embodiments, the one or more light intensity sensors comprise configuration to be anchored to the bottom of the body of liquid. In some embodiments, the one or more light intensity sensors comprise configuration to float on the aqueous liquid. In some embodiments, the one or more light intensity sensors comprise configuration to be connected to each other via one or more arms. In some embodiments, the one or more light intensity sensors comprise configuration to be connected to a shield.

In some embodiments, the one or more measurement device comprises configuration to be anchored to the bottom of the body of liquid. In some embodiments, the one or more measurement device comprises configuration to float on the aqueous liquid.

In some embodiments, systems and methods described herein comprise more than one measurement device. In some embodiments, systems and methods described herein comprise one or more, two or more, three or more, four or more measurement devices. In some embodiments wherein more than one measurement device is used, each measurement device may be positioned in a different location in a body of liquid. Systems and methods for measuring an aquatic biomass described herein comprising one of one or more, two or more, three or more, or four or more measurement devices are as shown in FIG. 7.

Further Embodiments

In further embodiments, the present invention and its embodiments relate to systems and method for measuring mat density of *Lemna* and for analyzing the distribution of *Lemna*, the crop health of *Lemna*, and the protein concentration of *Lemna*.

A first embodiment of the present invention describes a method to measure a mat density of *Lemna*. The method includes numerous process steps, such as: inserting a device at a location in a pond to obstruct a superficial flow of *Lemna* such that the *Lemna* compiles at an area upstream from the device. In examples, the pond is a raceway-shaped pond and the device is an obstruction mechanism. In preferred examples, the device is a mechanical obstruction mechanism. In other examples, the device may be a tube, a bar, a plate, or a combination thereof. In some examples, the device may float and in other examples, the device may be submerged. The method then includes: utilizing one or more sensors to determine a total surface area covered by the *Lemna* during a time period without taking physical samples, where a distribution of the *Lemna* over the total surface area depends on an amount of the *Lemna* such that similar amounts of the *Lemna* cover similar areas. Further, the total surface area covered by the *Lemna* depends on the amount of the *Lemna*. Additionally, the method includes measuring a total mat thickness and other parameters that used to assess total *Lemna* biomass, such as density of leaf tissue and optical characteristics, including leaf size and color. In some examples, one or more sensors comprises one or more optical sensors. In preferred examples, the one or more optical sensors comprise one or more cameras.

In some examples, the one or more sensors may be further configured to determine a distribution pattern of the *Lemna* into the device from when the device is inserted at the location until the *Lemna* has compiled behind the device and has reached a stable state covering a stable surface area.

In other examples, the one or more sensors may be further configured to determine a redistribution pattern of the *Lemna* when the device is removed.

In additional examples, the method may further include utilizing a first set of sensors located above the *Lemna* and water of the pond and a second set of sensors located in the water of the pond to measure a light intensity (lux) differential. In some examples, the first set of sensors and the second set of sensors comprise light sources that use specific wavelengths of the spectrum. In other examples, the first set of sensors and the second set of sensors comprise photosynthetically active radiation (PAR) sensors.

In some examples, a first subset of the first set of sensors and a first subset of the second set of sensors are located in the area upstream from the device. A second subset of the first set of sensors and a second subset of the second set of sensors are located in other locations in the pond. The first subset of the first set of sensors, the second subset of the first set of sensors, the first subset of the second set of sensors, and the second subset of the second set of sensors comprise configuration to capture one or more images to determine a decreasing density of the *Lemna* when it is compiling in the area upstream from the device and when the *Lemna* is redistributing on the surface of the pond. In examples, additional light sources (e.g., LED lights and/or lasers) may be used in combination with the aforementioned sensors to make the quantification more robust and less dependent on the solar output.

The method described herein may further include: determining a weight measurement of the *Lemna* in the total surface area, estimating a total amount of *Lemna* in the pond, and calculating a mat density of *Lemna*. Additional data points may also be incorporated into the calculation of the mat density of *Lemna*, such as: the distribution pattern, the redistribution pattern, the lux differential, and/or the decreasing density of the *Lemna*, among other data points not explicitly listed herein. Further, the method may include measuring the mat density of the *Lemna* using Normalized Difference Vegetation Index (NDVI) technology.

A second embodiment of the present invention describes a system to measure a mat density of *Lemna*. The system includes at least a mechanical obstruction mechanism and one or more sensors. In some examples, the one or more sensors comprise a first set of sensors located above the *Lemna* and water of the pond and a second set of sensors are located in the water of the pond. The second set of sensors may be underwater sensors located at varying depths in the water of the pond. In a first example, the first set of sensors and the second set of sensors comprise light sources that use specific wavelengths of the spectrum. In a second example, the first set of sensors and the second set of sensors comprise photosynthetically active radiation (PAR) sensors.

The mechanical obstruction mechanism is inserted at a location in a pond of water to obstruct a superficial flow of *Lemna* such that the *Lemna* compiles at an area upstream from the mechanical obstruction mechanism.

The one or more sensors comprise configuration to: determine a total surface area covered by the *Lemna* during a time period without taking physical samples, where a distribution of the *Lemna* over the total surface area depends on an amount of the *Lemna* such that similar amounts of the *Lemna* cover similar areas. Further, the one or more sensors comprise configuration to: determine a distribution pattern of the *Lemna* into the mechanical obstruction mechanism from when the mechanical obstruction mechanism is inserted at the location until the *Lemna* has compiled behind the mechanical obstruction mechanism and has reached a stable state covering a stable surface area and determine a redistribution pattern of the *Lemna* when the mechanical obstruction mechanism is removed.

In some examples, the first set of sensors and the second set of sensors comprise configuration to measure a light intensity (lux) differential. In another example, a first subset of the first set of sensors and a first subset of the second set of sensors are located in the area upstream from the device. A second subset of the first set of sensors and a second subset of the second set of sensors are located in other locations in the pond. The first subset of the first set of sensors, the second subset of the first set of sensors, the first subset of the second set of sensors, and the second subset of the second set of sensors comprise configuration to capture one or more images to determine a decreasing density of the *Lemna* when it is compiling in the area upstream from the device and when the *Lemna* is redistributing on the surface of the pond.

The system may comprise light sensors placed above the water surface and at the bottom of the pond with an additional obstruction device that will prevent *Lemna* mat forming above the sensor placed at the bottom of the pond. These sensors may be useful to quantify the amount of algae present in the water column. Correction for algae present in the water column may be useful in mat density calculations to increase the accuracy of the method.

Using the system, a weight measurement of the *Lemna* in the total surface area is determined, a total amount of *Lemna* in the pond is determined, and a mat density of the *Lemna* and a total protein content is calculated. Other data points may be incorporated into the determination of the mat density of the *Lemna*, such as: the distribution pattern, the redistribution pattern, the lux differential, and/or the decreasing density of the *Lemna*, among other data points not explicitly listed herein.

Duckweed belongs to the Lemnaceae family. The terms "*lemna*" and "duckweed" may be used interchangeably herein. Duckweed is composed of small-sized monocotyledon plants floating on the surface of stagnant or low water velocity pools, where water is rich in nutrients. The plant structure of duckweed is relatively simple, devoid of distinct roots, stalks or leaves. The worldwide spread of duckweed is due to its genetic adaptation, which leads to a wide variety of different species.

The Lemnaceae family includes four main families, namely *Lemna, Spirodela, Wolffia* and Wolfiella. About 40 species of duckweed have been inventoried worldwide in various aquatic environments. Duckweed displays fast reproduction through gemmation and absorbs large amounts of nutrients such as nitrogen (N) and phosphorus (P).

Under natural conditions, it is possible to see a mat or carpet of duckweed that explodes in a growth pattern. In fact, *Lemna* will distribute itself on the surface area of a pond towards where water current takes it, and where it will be easy for the floating biomass to go. The distribution of the total biomass is very unevenly spread over the total surface area of the pond, and distribution is not linear when total biomass in a pond varies, which complicates using samples from single or multiple spots as a reference for the estimation of total biomass.

Biotic and abiotic factors, such as water temperature, concentration of minerals in the water, water pH, incidence of sunlight, and mat density exert an effect on duckweed growth. Specifically, duckweed grows at temperatures as low as 1-3° C. and will survive light freezes and even continue to grow during the winter months. Duckweed growth is optimal at temperatures between 20 and 30° C. and the productivity/growth rate of the duckweed is negatively impacted. Below 17° C. some duckweeds show a decreasing rate of growth. Duckweed tolerates a wide range of pH (3.0-10.0), but displays optimum growth in a medium of 5.0-7.0.

Duckweed is being studied by researchers around the world as a possible source of clean energy and for biomanufacturing purposes. Duckweed is a good candidate as a biofuel because it grows rapidly, produces five to six times as much starch as corn per unit of area, and does not contribute to global warming.

For operational purposes, it is important to understand the quantity of *Lemna* in a pond system at a given point in time to properly manage the timing of harvest, dosing of nutrients and controlling other factors that influence productivity and quality of the crop. Further, as explained, *Lemna* will distribute itself on the surface area of a pond towards where water current takes it, and where it will be easy for floating biomass to go, which means that distribution of the total biomass is very unevenly spread over the total surface area of the pond, and distribution is not linear when total biomass in a pond varies, which complicates using samples from single or multiple spots as a reference for the estimation of total biomass.

Another exemplary method and a system to measure a mat density of *Lemna* are described and depicted in FIG. 4, FIG. 5, and FIG. 6 herein. The system includes an obstruction device 148. In some examples, the obstruction device 148 is a mechanical obstruction mechanism. In preferred examples, the obstruction device 148 is an automated mechanical obstruction mechanism. In other examples, the obstruction device 148 may be a tube, a bar, a plate, or a combination thereof. In some examples, the obstruction device 148 may float and in other examples, the obstruction device 148 may not float. In some examples, the system continuously monitors the mat density in the pond 144 when no obstruction mechanism or device 148 is used.

It should be appreciated that the obstruction device 148 is inserted at a location in a pond 144 of water 146 to obstruct a superficial flow of *Lemna* 150 such that the *Lemna* 150 compiles at an area upstream from the obstruction device 148. In examples, the pond 144 comprises a raceway-shape. The *Lemna* 150 may be collected over an area upstream from the obstruction device 148.

The system also includes one or more sensors. As shown in FIG. 6 and FIG. 7, an area above a surface of a pond 144 is denoted 152 and an area below the surface 156 of the pond 144 is denoted 158. In some examples, the one or more sensors comprise a first set of sensors 154 located above the surface 152 of the pond 144 and above the *Lemna* 150. A second set of sensors 154 are located in the water 146 below the surface 152 of the pond 144.

In a first example, the first set of sensors 154 and the second set of sensors 158 comprise light sources that use specific wavelengths of the spectrum. In a second example, the first set of sensors 154 and the second set of sensors 158 comprise photosynthetically active radiation (PAR) sensors. It should be appreciated that PAR sensors comprise configuration to measure photosynthetic light levels in both air and water and reports the Photosynthetic Photon Flux Density (PPFD), which corresponds to micromoles of photons per meter squared per second (umol $m^{-2}$ $s^{-1}$).

In general, the one or more sensors 154, and 158 of the system comprise configuration to: determine a total surface area covered by the *Lemna* 150 during a time period without taking physical samples. A distribution of the *Lemna* 150 over the total surface area depends on an amount of the *Lemna* 150 such that similar amounts of the *Lemna* 150 cover similar areas (e.g., more *Lemna* 150 covers a larger surface area than less *Lemna* 150). Further, the one or more sensors 154 and 158 comprise configuration to: determine a distribution pattern of the *Lemna* 150 into the obstruction device 148 from when the obstruction device 148 is inserted at the location until the *Lemna* 150 has compiled behind the obstruction device 148 and has reached a stable state covering a stable surface area. Furthermore, the one or more sensors 154 and 158 comprise configuration to: determine a redistribution pattern of the *Lemna* 150 when the obstruction device 148 is removed. The data points of the distribution pattern and/or the redistribution pattern may be incorporated into a determination of the mat density of the *Lemna* 150 to improve the accuracy of such determination.

In some examples, the first set of sensors 154 and the second set of sensors 158 comprise configuration to measure a light intensity (lux) differential. The natural ambient light will be fully captured by the first set of sensors 154. The light intensity captured by the second set of sensors 158 in the water 146 will determine a lower light intensity. The lux differential may also be incorporated into the determination of the mat density of the *Lemna* 150 to improve the accuracy of such determination.

In another example, a first subset 162 of the first set of sensors 154 and a first subset 164 of the second set of sensors 158 are located in the area upstream from the obstruction device 148. A second subset 166, 168 of the first set of sensors 154 and a second subset 170, 172 of the second set of sensors 158 are located in other locations in the pond 144. The first subset 162 of the first set of sensors 154, the second subset 166, 168 of the first set of sensors 154, the first subset 162 of the first set of sensors 154, and the second subset 170, 172 of the second set of sensors 158 comprise configuration to capture one or more images to determine a decreasing density of the *Lemna* 150 when it is compiling in the area upstream from the obstruction device 148 and when the *Lemna* 150 is redistributing on the surface of the pond 144. These data points may also be incorporated into the determination of the mat density of the *Lemna* 150.

Using the system described herein, since the *Lemna* 150 distribution takes place on an area of which the total surface area is known, actual weight measurements are taken to validate the consistency of the weight when *Lemna* 150 covers a certain area. The total surface area covered by the *Lemna* 150 when obstructed by the obstruction device 148 can therefore be used as a proxy to accurately estimate the total amount of the *Lemna* 150 in the pond 144. The mat density of the *Lemna* 150 may also be calculated. As described, other data points may be incorporated into the determination of the mat density of the *Lemna* 150.

In some implementations, the system may further utilize Normalized Difference Vegetation Index (NDVI) technology. As described herein, NDVI is a graphical indicator that can be used to analyze remote sensing measurements, assessing whether or not the target being observed contains live green vegetation. The local mat density may be measured using the NDVI technology to determine the reflection of near infrared light by the *Lemna* 150 on the surface 152, which can provide additional insight regarding density of the *Lemna* 150 in thicker areas of the total surface area where all of the *Lemna* 150 compiles behind the obstruction device 148. It should be appreciated that prior observations have shown that just the length of the *Lemna* 150 behind of the obstruction device 148 is an accurate indicator of total biomass given a constant water flow rate, and consistent biomass quality. However, accuracy can further be increased when a single density measurement just in front of the obstruction device 148 is taken, from where the *Lemna* mat generally shows a linear decline in mat density towards an end of the *Lemna* mat. Therefore, considering that the obstruction device 148 may always be placed in the same spot in a greenhouse, a spot sensor measuring the thickest area will be easy to implement and a source of consistent density measurements when the obstruction device 148 is in place.

In other examples, the present invention provides a technique for rapid superficial *Lemna* accumulation for harvesting. One of the challenges in harvesting the *Lemna* is to quickly remove large quantities of the *Lemna* from a pond system, without also removing a lot of water at the same time. The key in managing this is to maintain a high density of the *Lemna* at the location where harvesting takes place. During harvesting operations, a continuous supply of the *Lemna* over the surface of the water is necessary to keep densities of the *Lemna* high and to support continuous high harvesting rates. Increasing water flow rate contributes to faster superficial supply of the *Lemna*, but has limitations due to creation of waves, energy consumption, and decreasing effectiveness of the obstruction pipe. Also, the accumulation of very high densities makes the *Lemna* flow slower, because the thick mat starts to inhibit its own mobility and flow rate on the surface. Continuous supply of more moderate densities of the *Lemna* leads to higher amounts of the *Lemna* supplied to the target harvesting spot in the same time, and can be achieved by using water flow under the mat density that pulls the *Lemna* along. This water flow can be increased by using a simple, static underwater find mounted down vertically from the obstruction pipe or device, allowing more or less water flow in different areas where the obstruction pipe is blocking the *Lemna*. Using this technique, larger amounts of the *Lemna* can be supplied to spots where that is desired, without addition energy requirements or other mechanical (moving) adjustments.

EXAMPLES

The following examples are included for illustrative purposes only and are not intended to limit the scope of the invention.

Example 1: Aquatic Biomass Mat Density Measurement Device

A mat density measurement device (MDM device) was developed to calculate the mat density of growing *Lemna*. The MDM device included a shield and three light sensors as shown in FIG. 1. Referring to FIG. 3, the light sensors were configured to be positioned above an aqueous liquid and aquatic biomass surface (A), below an aqueous liquid and aquatic biomass surface (C), and in an area of the aqueous liquid column that is substantially free of the aquatic biomass (D). In this example, *Lemna minor* was used as the aquatic biomass. Each light sensor measured light intensity in lux in its respective field of measurement (i.e., above aquatic biomass (A), below aquatic biomass (C) or in aquatic biomass-free aqueous liquid (D)) and the respective values were inserted into Equation 1 (below) to calculate the Absorption Coefficient of aquatic biomass (*Lemna minor* here). Equation 1 is below.

$$\text{Absorption Coefficient}(X) = \ln\frac{A}{C} - \ln\frac{A}{D}$$

Without being bound by theory, it was contemplated that light intensity from above the aqueous liquid *Lemna* surface (A) decreased rapidly as it passed through the floating layer of *Lemna minor* (B) into the aqueous liquid column (C) because it was absorbed by *Lemna minor* pigments. The Absorption Coefficient was determined from establishing the light intensity differential between the *Lemna minor* covered aqueous liquid column (C) and the *Lemna minor* free aqueous liquid column (D) as shown in Equation 1. Mat Density was then correlated to the Absorption Coefficient (X) as shown in Equation 2 below where $Z_1$ and $Z_2$ were correlation coefficients obtained by fitting a line through a series of points (e.g., data points for weighted mat density and absorption coefficient). Equation 2 is below.

$$\text{Mat Density }(Y) = (Z_1 \times X) + Z_2$$

Once past the *Lemna* layer, light intensity still slowly decreased in the aqueous liquid column (C) due to multiple factors, such as algae. It was also contemplated that another intervening variable for optically determining biomass density was aqueous liquid turbidity measured in *Lemna minor* free aqueous liquid column (D). Accordingly, to generate a reliable model for establishing *Lemna minor* mat density, and to reduce noise, forward and reverse calibrations were carried out to generate correlation coefficients—$Z_1$ and $Z_2$.

Example 2: Forward Calibration of the Correlation Coefficients

To calibrate Equation 2, a forward calibration was performed in a watertight 22 m² pond with a depth of about 10 cm to about 50 cm configured to hold aqueous liquid at a temperature of about 10° C. to about 40° C. at a pH of about 5 to about 7. A propulsion mechanism in the pond generated a circulating aqueous liquid flowing at a rate of about 0.01 meters/second to about 1 meter/second. Known amounts of weighed *Lemna minor* were added incrementally to the pond in 45 to 60 minute intervals until mat density reached about 1400 g/m² (TABLE 3). Scheduled and actual inoculation time was recorded for each inoculation. While inoculated *Lemna minor* amounts were known (Actual Inoculation Amount (AIA)), the AIA (and therefore actual mat density) differed from the Target Inoculation Amount (TIA). To avoid deviating from the Target Running Amount (TRA), and therefore not measuring the mat densities planned, a New Target Inoculation Amount (NTAI) was calculated after each inoculation as shown in Equation 3 below where the Actual Running Amount (ARA) was calculated as the sum of the AIAs. Equation 3 is below.

$$NTIA = TIA + (TRA - ARA)$$

Light intensity measurements were acquired 15 minutes after each inoculation (addition) of weighed *Lemna minor* to allow for even distribution of *Lemna minor* in the pond. Absorption coefficient values, or the amount of light absorbed by *Lemna minor*, was calculated using the light intensity measurements in Equation 1 and correlated to weighed mat density as seen in TABLE 3.

TABLE 3

Mat Density of Growing Aquatic Plant v. Absorption Coefficient

| Weighed Mat Density ($g/m^2$) | Absorption Coefficient (Au) |
|---|---|
| 0 | 0.0 |
| 212 | 0.4 |
| 427 | 1.2 |
| 646 | 1.9 |
| 882 | 2.7 |
| 1110 | 3.6 |
| 1378 | 4.3 |

Figure 8:
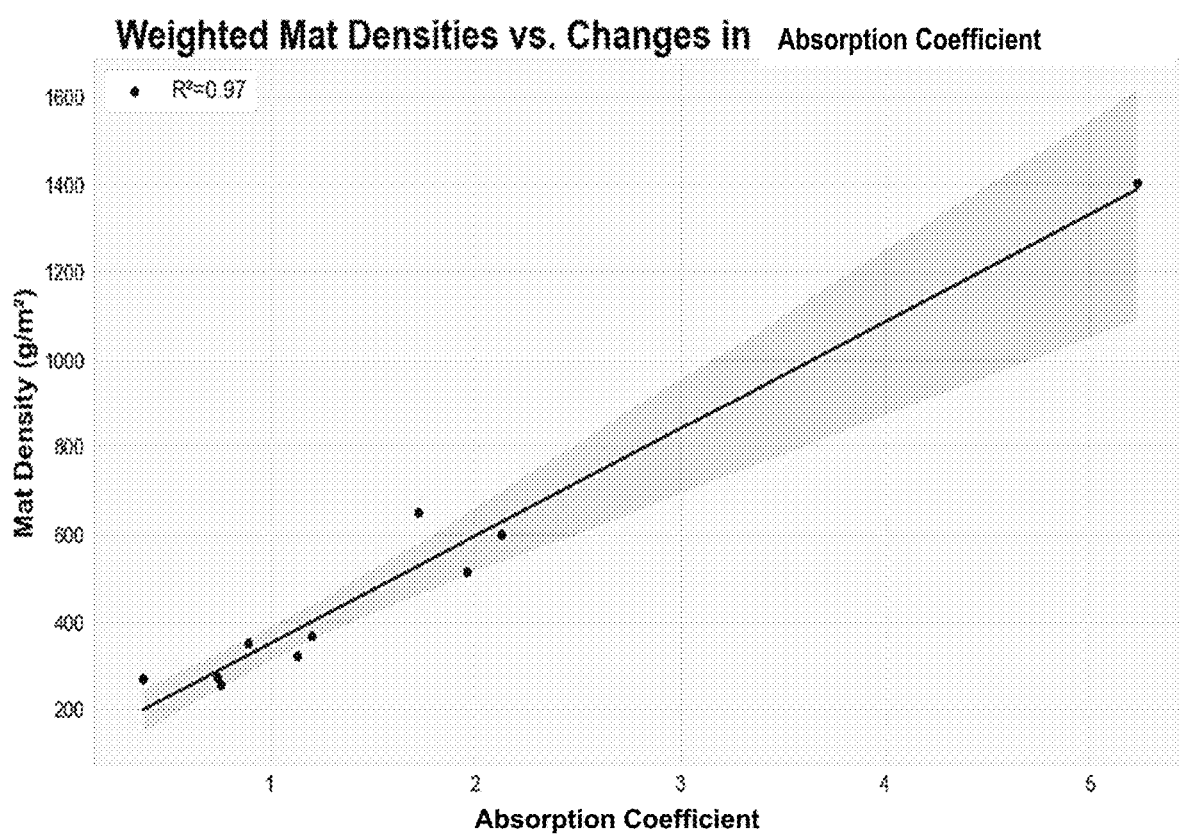
FIG. 8 illustrates a relationship between light absorption coefficient and mat density measurements ($g/m^2$).

Weighed mat density (in $g/m^2$) was plotted against absorption coefficient values (in absorption units or Au). As seen in FIG. 8, a linear regression model was generated using Python 3.0 for curve fitting and to determine correlation coefficients—$Z_1$ and $Z_2$. A $R^2$ analysis was performed ($R^2=0.97$), as shown in FIG. 8, to establish how well the regression model fits the data. The data demonstrates that there is a statistically significant correlation between Mat Density and the Absorption Coefficient.

Example 3: Reverse Calibration of the Mat Density/Absorption Coefficient Curve

An MDM system was set up to identify the most optimal location for sensor placement. Multiple MDM devices were distributed in a 250 $m^2$ running pond used for *Lemna* growth (FIG. 7). *Lemna minor* was harvested in 90 minute increments until no *Lemna* was present. Weights were taken in aqueous liquid draining barrels at least 30 minutes after post harvest wash.

Each scheduled harvest had a Target Harvest Amount (THA) measured in grams. The Actual Harvest Amount (AHA) and therefore the actual mat densities would differ from the target, so these actual values were recorded. To avoid deviating from the Target Running Amount (TRA), and therefore not measuring the mat densities planned, a New Target Harvest Amount (NTHA) was calculated after each harvest as shown in Equation 4 below where the Actual Running Amount (ARA) is calculated as Starting Running Amount–Sum of AHAs. Equation 4 is below.

$$NTHA = THA + (TRA - ARA)$$

At each harvest, *Lemna minor* was temporarily blocked with a 4 inch or 6 inch polyvinyl chloride (PVC) pipe floated across the running pond flow. The time point at which the PVC pipe block was removed from the pond was recorded as the block release time. In between blocks and removals, the remaining *Lemna minor* was evenly distributed in the pond. Light intensity measurements were acquired 15 minutes after each block release time.

Data from each MDM device was used to calculate the absorption coefficient for each known amount of *Lemna minor* removed from the pond and the mean absolute error calculated (TABLE 4).

TABLE 4

Absorption Coefficients of MDM Devices 1 2, 3, and 5

| MDM Device | Absorption Coefficient | MAE |
|---|---|---|
| 1 | 517.9794 | 27 |
| 2 | 639.7212 | 40 |
| 3 | 453.6014 | 118 |
| 4 | — | — |
| 5 | 577.9511 | 66 |

Figure 9:
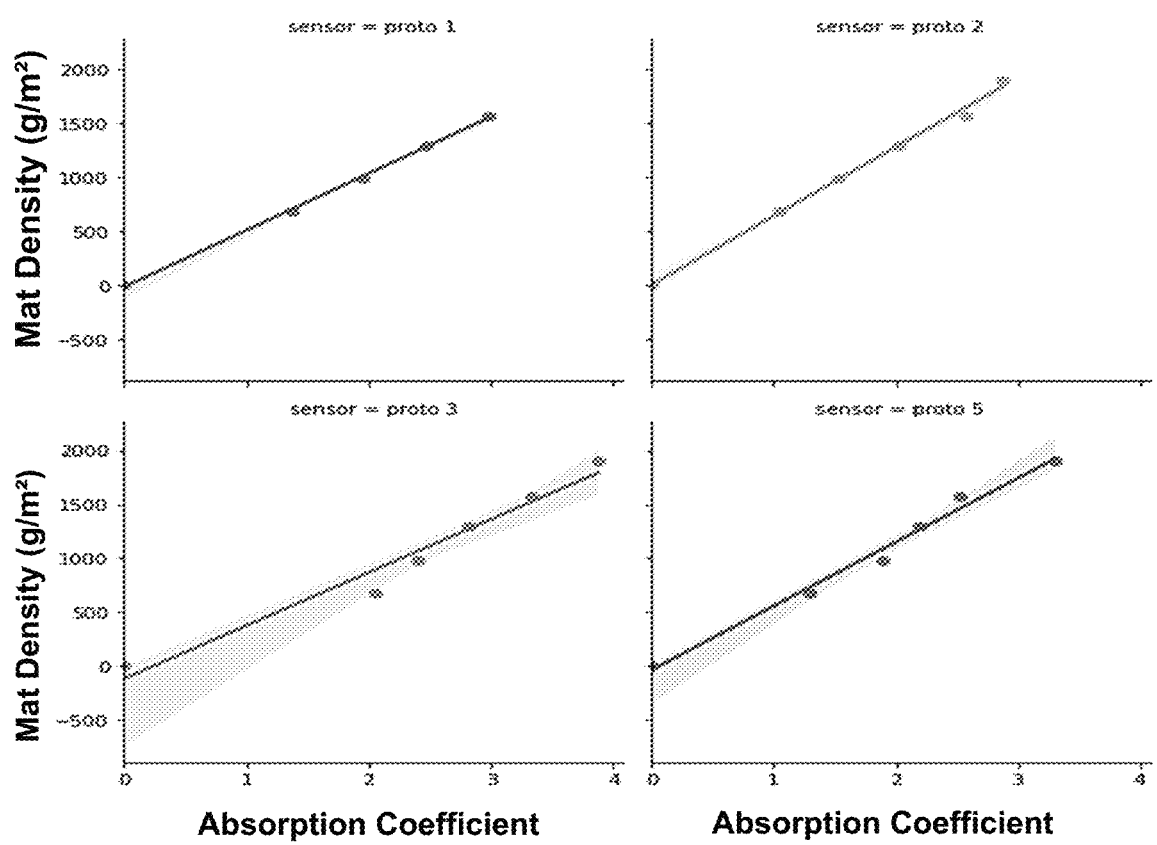
FIG. 9 illustrates a relationship between light absorption coefficient and mat density measurements ($g/m^2$), as derived from 4 measurement devices in the system shown in FIG. 7.
Figure 10:
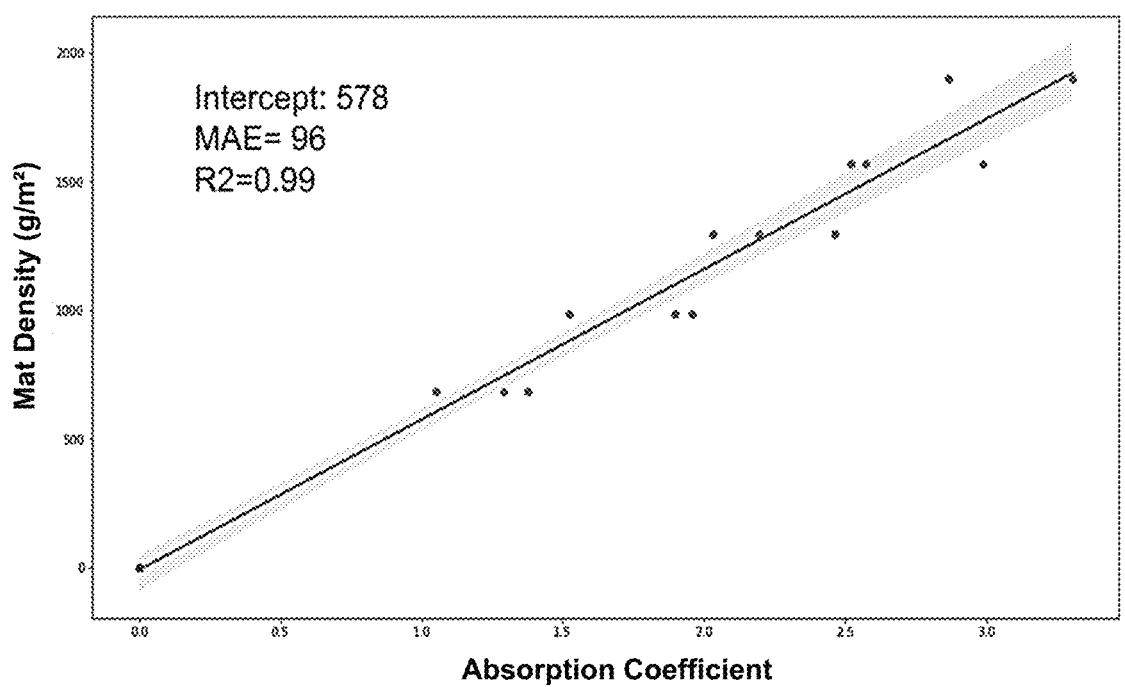
FIG. 10 illustrates the average relationship between light absorption coefficient and mat density measurements ($g/m^2$) utilizing data as combined for the 4 measurement devices as shown in FIG. 7 and plotted in FIG. 9.

The data from each device was collected and plotted (FIG. 9). The data for three of the MDM devices (i.e., MDM device 1, 2, and 5) was combined and plotted. The curve was calibrated using Python 3.0 and a linear regression analysis ($R^2=0.99$) was performed (FIG. 10). The data demonstrates that the Mat Density/Absorption Coefficient Curve (Equation 2) is statistically significant.

Example 4: Protein Isolation and Purification

Example 4.1: Workflow A

One kg of fresh *Lemna minor* was macerated in a Vitamix Blender (Vitamix Corp, Cleveland, Ohio) in a ratio of 1:1 with a sodium carbonate buffer containing 0.3% w/v sodium bisulfite. The extraction was performed for 3 minutes at medium speed setting maintaining the temperature at less than 30° C. Subsequently, the macerated biomass was filtered by using a nylon straining bag (Natural Home Brands, Sun Valley, California) with a fine mesh to separate the fibrous high solids cake from the liquid juice containing the soluble protein. The filtered homogenate was then centrifuged for 10 minutes at a speed/force of 4000 g (Allegra X15R, SX4750 rotor; Beckman Coulter, Inc., Pasadena, California). The pellet was discarded, and the supernatant was collected separately. The solution was heated to a temperature of 50° C. in a aqueous liquid bath that was set at a temperature of 55° C. and was cooled rapidly to a temperature less than 15° C. after reaching the target temperature. Following the rapid cooling of the protein solution, 2% v/v of activated chitosan and 4% w/v of activated carbon (Cabot Norit Americas Inc, Marshall, Texas) is added to the liquid juice. The solution was subsequently stirred for 5 minutes after which the solution was centrifuged for 10 minutes at a speed/force of 5000 g (Allegra X15R, SX4750 rotor; Beckman Coulter, Inc., Pasadena, California). The green pellet in the centrifuge bottle was discarded, and the clear yellow supernatant was micro filtered using a 0.7 pm Glass Micro fiber membrane (Whatman 1825-047 Glass Microfiber Binder Free Filter, 0.7 Micron; Global Life Sciences Solutions USA LLC, Marlborough, Massachusetts). The filtrate was subsequently exposed to a 0.2 pm polyethersulfone membrane (Polyethersulfone (PES) Membrane Filters, 0.2 Micron; Sterlitech Corporation Inc, Kent, Washington) to remove the remainder of the undesired particles including bacteria. The obtained pale yellow and deodorized proteinaceous solution was then concentrated using a 70 kDa membrane (MINIKROS® S02-E070-05-N; Spectrum Laboratories, Inc., Rancho Dominguez, California). The concentrated solution obtained was subsequently freeze dried (Harvest Right LLC, Salt Lake City, Utah) and the result was a white, odorless and soluble protein powder.

Example 4.2: Workflow B

One kg of fresh *Lemna minor* was macerated using a Vitamix Blender (Vitamix Corp, Cleveland, Ohio) in a ratio of 1:1 with a potassium phosphate buffer containing 0.3% w/v ascorbic acid. The maceration was performed for a period of 3 minutes at medium speed in order to maintain a temperature of less than 30° C. The lysed biomass was filtered by using a nylon straining bag (Natural Home Brands, Sun Valley, California) with a fine mesh to separate the fibrous high solids cake from the liquid juice containing the soluble protein. The filtered homogenate was then centrifuged for 10 minutes at a speed/force of 4000 g (Allegra X15R, SX4750 rotor; Beckman Coulter, Inc., Pasadena, California). The pellet was discarded, and the supernatant was collected separately. The supernatant was then mixed with 5% v/v of activated chitosan (Chitosan (10-120 cps), fungal origin (9012-76-4); Glentham Life Sciences Ltd., Corsham, Wiltshire, UK) and 10% w/v of activated carbon (Cabot Norit Americas Inc, Marshall, Texas) for a period of 5 minutes. Subsequently the mixed solution was centrifuged at a speed/force of 5000 g for 10 minutes (Allegra X15R, SX4750 rotor; Beckman Coulter, Inc., Pasadena, California). The obtained pellet was discarded, and the deodorized and decolored supernatant was microfiltered using a 0.2 pm polyethersulfone membrane (Polyethersulfone (PES) Membrane Lilters, 0.2 Micron; Sterlitech Corporation Inc, Kent, Washington). The obtained pale yellow and deodorized proteinaceous solution was then concentrated using a 70 kDa membrane (MINIKROS® S02-E070-05-N; Spectrum Laboratories, Inc., Rancho Dominguez, California). The concentrated solution obtained was subsequently freeze dried (Harvest Right LLC, Salt Lake City, Utah) and the result was a white, odorless and soluble protein powder.

Example 4.3: Workflow C

One kg of fresh *Lemna minor* was macerated using a Vitamix Blender (Vitamix Corp, Cleveland, Ohio) in a ratio of 1:1 with distilled aqueous liquid containing 0.3% w/v of sodium bisulfite and ascorbic acid. The maceration was performed for a period of 3 minutes at medium speed in order to maintain a temperature of less than 30° C. The lysed biomass was filtered by using a nylon straining bag (Natural Home Brands, Sun Valley, California) with a fine mesh to separate the fibrous high solids cake from the liquid juice containing the soluble protein. The filtered homogenate was then centrifuged for 10 minutes at a speed/force of 4000 g. The pellet was discarded, and the supernatant was collected separately. The supernatant was then mixed with a solution containing 30 mM of potassium phosphate and 20 mM of calcium chloride for a period of 5 minutes. Subsequently the mixed solution was centrifuged at a speed/force of 5000 g for 10 minutes (Allegra X15R, SX4750 rotor; Beckman Coulter, Inc., Pasadena, California). The obtained pellet was discarded. 5% w/v of activated carbon (Cabot Norit Americas Inc, Marshall, Texas) was added to the supernatant, and the solution was stirred for 5 minutes. Subsequently, the mixed solution containing the activated carbon was micro filtered using a 0.2 pm polyethersulfone membrane filter (Polyethersulfone (PES) Membrane Filters, 0.2 Micron; Sterlitech Corporation Inc, Kent, Washington) in order to remove the activated carbon that had adsorbed the remaining chlorophyll, polyphenol and other unwanted taste/color/odor impacting particles. The obtained pale yellow and deodorized proteinaceous solution was then concentrated using a 100 kDa membrane (Hollow Fiber Cartridge, 100,000 NMWC, 850 cm2; GE Healthcare Bio-Sciences Corp, Westborough, Massachusetts). The concentrated solution obtained was subsequently freeze dried and the result was a white, odorless and soluble protein powder.

Example 4.4: Workflow D

One kg of fresh *Lemna minor* was macerated using a Vitamix Blender (Vitamix Corp, Cleveland, Ohio) in a ratio of 1:1 with distilled aqueous liquid containing 0.5% w/v of sodium bisulfite. The maceration was performed for a period of 3 minutes at medium speed in order to maintain a temperature of less than 30° C. The lysed biomass was filtered by using a nylon straining bag (Natural Home Brands, Sun Valley, California) with a fine mesh to separate the fibrous high solids cake from the liquid juice containing the soluble protein. The filtered homogenate was then centrifuged for 10 minutes at a speed/force of 4000 g (Allegra X15R, SX4750 rotor; Beckman Coulter, Inc., Pasadena, California). The pellet was discarded, and the supernatant was collected separately. The supernatant was then mixed with a solution containing 30 mM of potassium phosphate and 20 mM of calcium chloride for a period of 5 minutes. Subsequently the mixed solution was centrifuged at a speed/force of 5000 g for 10 minutes (Allegra X15R, SX4750 rotor; Beckman Coulter, Inc., Pasadena, California). The obtained pellet was discarded. 2% w/v of activated chitosan (Chitosan (10-120 cps), fungal origin (9012-76-4); Glentham Life Sciences Ltd., Corsham, Wiltshire, UK) and 4% of activated carbon (Cabot Norit Americas Inc, Marshall, Texas) were added to the supernatant, and the solution was stirred for 5 minutes. Subsequently the mixed solution was centrifuged at a speed/force of 5000 g for 10 minutes (Allegra X15R, SX4750 rotor; Beckman Coulter, Inc., Pasadena, California). The obtained pellet was discarded, and the deodorized and decolored supernatant was microfiltered using a 0.7 pm polyethersulfone membrane (Whatman 1825-047 Glass Microfiber Binder Free Filter, 0.7 Micron; Global Life Sciences Solutions USA LLC, Marlborough, Massachusetts). The filtrate was then further microfiltered using a 0.2 pm polyethersulfone membrane (Polyethersulfone (PES) Membrane Filters, 0.2 Micron; Sterlitech Corporation Inc, Kent, Washington). The obtained pale yellow and deodorized proteinaceous solution was then concentrated using a 70 kDa membrane (MINIKROS® S02-E070-05-N; Spectrum Laboratories, Inc., Rancho Dominguez, California). The concentrated solution obtained was subsequently freeze dried (Harvest Right LLC, Salt Lake City, Utah) and the result was a white, odorless and soluble protein powder.

Example 4.5: Purity Analysis from Workflows A-D

The average purity of the protein preparations prepared by the methods of Workflows A-D was about 84.3% and the concentration of soluble protein after ultrafiltration was 1,316 pg/mL. The foaming capacity achieved was 195% and maintained a 92% stability after 1 hour. Gelation properties of the freeze-dried material were validated, and only 2% w/v of freeze-dried material was needed to be added in order to form a gel.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for measuring aquatic biomass, the method comprising:

flowing aqueous liquid and aquatic biomass in a pond;

measuring light absorption of a portion of the aquatic biomass, wherein the measuring comprises use of a measurement device, wherein the measurement device comprises:

a shield, wherein the shield obstructs flow of the biomass in an area adjacent to a shield; and light intensity sensors, wherein the light intensity sensors comprise at least three light intensity sensors, wherein the light intensity sensors collect measurements of light intensity:

at a comparator region located above a surface of the aqueous liquid;

at a flow obstruction region located below a surface of the aqueous liquid in an area substantially free of an aquatic biomass; and at a biomass region located below a surface of the aqueous liquid; and determining a value for mass, surface area, density, or combinations thereof of the aquatic biomass in the pond.

2. The method of claim 1, wherein the determining further comprises calculating, based on light intensity, the light absorption of a portion of the aquatic biomass.

3. The method of claim 1, wherein the light intensity sensors comprise optical sensors.

4. The method of claim 3, wherein the optical sensors each comprise a light meters lux meter, a UV meter, a photosynthetically active radiation (PAR) sensor, a camera, or a combinations thereof.

5. The method of claim 3, wherein the optical sensors measure photometric units.

6. The method of claim 3, wherein the optical sensors measure lumens per unit area.

7. The method of claim 3, wherein the optical sensors measure lux or lumens per square meter.

8. The method of claim 3, wherein the optical sensors comprise lux meters.

9. The method of claim 3, wherein the optical sensors comprise light meters.

10. The method of claim 4, wherein the camera comprises a digital camera, non-digital camera, integrated camera, single camera, dual camera, timer-specific camera, or combinations thereof.

11. The method of a claim 3, wherein the optical sensors comprise photosynthetically active radiation (PAR) sensors.

12. The method of claim 1, wherein the light intensity sensors measure light absorption at 10 nanometers to 400 nanometers wavelength.

13. The method of claim 1, wherein the light intensity sensors measure light absorption at 400 nanometers to 700 nanometers wavelength.

14. The method of claim 1, wherein the light intensity sensors measure light absorption at 750 nanometers to 10,000 nanometers wavelength.

15. The method of claim 2, wherein a light intensity differential is obtained from measurements of light intensity.

16. The method of claim 15, wherein a light intensity differential calculated from a difference between a ratio of light intensity at a comparator region located above a surface of the aqueous liquid to light intensity at a biomass region below a surface of the aqueous liquid in an area not substantially free of an aquatic biomass, and a ratio of light intensity at a comparator region located above a surface of the aqueous liquid to light intensity at a biomass region below a surface of the aqueous liquid in an area in that is substantially free of an aquatic biomass.

17. The method of claim 16, wherein the light absorption is calculated from the light intensity differential.

18. The method of claim 1, wherein an aquatic biomass measurement is related to the measurement of light absorption.

19. The method of claim 18, wherein the measurement is density.

20. The method of claim 18, wherein the measurement is value of mass.

21. The method of claim 18, wherein the measurement is surface area.

22. The method of claim 1, wherein the flow is a circulating flow.

23. The method of claim 1, wherein the method comprises the use of one, two, three, four, five, or more measurement devices.

24. The method of claim 1, wherein the light intensity sensors to collect measurements of light intensity communicate data measurements to an imaging system or a computer system adapted to process the data, wherein the processing comprises calculations.

25. The method of claim 1, wherein the value for mass, surface area, density, or combinations thereof of the aquatic biomass in the pond is determined from one or more device.

26. The method of claim 1, wherein the aquatic biomass comprises *Lemna minor*.

27. The method of claim 1, wherein the aquatic biomass comprises an aquatic photosynthetic organism.

28. The method of claim 27, wherein the aquatic photosynthetic organism comprises a member of the Bacillariophyta, Chlorophyta, Chrysophyta, Euglenophyta, Euglenozoa, Paeophyta, *Porphyra*, Pyrrophyta, Rhodophyta, or Xanthophyta phylum, or combinations thereof.

29. The method of claim 27, wherein the aquatic photosynthetic organism comprises a member of the Caulerpaceae, Chlorophyta, Chrysophyta, Chrysophyceae, Cryptophyceae, Dinophyceae, Euglenophyceae, Fucaceae, Florideophyceae, Gigartinaceae, Gracilariaceae, Laminariaceae, Lemnaceae, Salviniaceae, Monostromataceae, Phaeophyceae, Ulvaceae, Xanthophyceae, or algae family, or combinations thereof.

30. The method of claim 27, wherein the aquatic photosynthetic organism comprises a member of the *Ankistrodesmus, Asteromonas, Azolla, Carteria, Chlamydomonas, Chlorella, Chlorococcum, Chlorogonium,* Chlorophyceace, *Chrysosphaera, Dunaliella, Euglena, Fucus, Furcellaria, Gracilaria, Haematococcus, Laminaria, Landoltia, Lemna, Macrocystis, Monoraphidium, Monostroma, Nannochloropsis, Neochloris, Oedogonium, Ochromona, Oscillatoria, Pelagomonas, Phormidium, Pleurococcus, Porphyra, Pyrobotrys, Sargassum, Scenedesmus, Selenastrum, Spirodela, Spirulina, Volvox, Wolffia,* or *Wolffiella* genus, or combinations thereof.

31. The method of claim 27, wherein the aquatic photosynthetic organism comprises *Lemna*.

32. The method of claim 31, wherein the *Lemna* comprises *Lemna aequinoctialis, Lemna disperma, Lemna ecuadoriensis, Lemna gibba, Lemna japonica, Lemna minuta, Lemna obscura, Landoltia punctata, Lemna perpusilla, Lemna tenera, Lemna trisulca, Lemna turionifera, Lemna valdiviana, Lemna yungensis, Spirodela polyrhiza, Wolffia arrhiza, Wolffia globosa*.

33. The method of claim 27, wherein the aquatic photosynthetic organism comprises *Azolla, Azolla caroliniana, Azolla cristata, Azolla filiculoides, Azolla imbricata, Azolla nilotica, Azolla pinnata, Azolla rubra,* or combinations thereof.

34. The method of claim 27, wherein the aquatic photosynthetic organism comprises *Ascophyllum nodosum, Botrydium, Caulerpa, Chondrus crispus,* Euglenoids, *Fucus, Fucus crispus, Fucus serratus, Fucus vesiculosus, Furcellaria lumbricalis, Gracilaria parvispora, Gracilaria tikvahiae, Laminaria digitata, Laminaria farlowii, Laminaria hyperborean, Laminaria nigripes, Macrocystis pyrifera, Monostroma kuroshiense, Monostroma latissimum, Monostroma nitidum, Prymnesium parvum, Palmaria palmata, Saccharina latissima, Tribonema, Ulva intestinalis, Vaucheria,* or combinations thereof.

35. The method of claim 27, wherein the aquatic photosynthetic organism comprises duckweed, duckweed fern, mosquito fern, water fern, fairy moss, and algae, or combinations thereof.

36. The method of claim 27, wherein the aquatic photosynthetic organism comprises lesser duckweed, minute duckweed, gibbous duckweed, common duckweed, ivy duckweed, least duckweed, Valdivia duckweed, rockweed, gutweed, green algae, golden algae, golden brown algae, golden brown algae and diatoms, fire algae, red algae, yellow-green algae, brown algae, single-cell algae, microalgae, macroalgae, kombu, kelp, sugarkelp, grass kelp, giant kelp, bladder kelp, sea oak, knotted kelp, knotted wrack, sea lettuce, serrated wrack, carrageen, forked seaweed, brown seaweed, dulse, dulce sol, or combinations thereof.

37. The method of claim 36, wherein the aquatic photosynthetic organism comprises a floating aquatic photosynthetic organism.

38. The method of claim 1, wherein the density comprises mat density.

39. The method of claim 38, wherein mat density is from about 750 g/m$^2$ to about 1500 g/m$^2$.

40. The method of claim 37, wherein the floating aquatic photosynthetic organism comprises a *Lemna* species.

41. The method of claim 1, wherein the aquatic biomass comprises a thickness of about 0.1 millimeters to about 5 millimeters.

42. The method of claim 1, wherein the aquatic biomass comprises a weight of about 100 grams per meter squared to about 3000 grams per meter squared.

43. The method of claim 1, further comprising the step of optimizing a growth of the aquatic biomass, wherein the method comprises adjusting a mass, surface area, or density, of the aquatic biomass based on the calculated mass, surface area, or density, thereby optimizing the growth of the aquatic biomass or aquatic photosynthetic organism.

44. The method of claim 43, wherein optimizing the growth of the aquatic biomass comprises adjusting aquatic biomass over a time interval.

45. The method of claim 43, wherein optimizing the growth of the aquatic biomass comprises adjusting aqueous liquid turbidity.

46. The method of claim 43, wherein optimizing the growth of the aquatic biomass comprises adjusting temperature, pH, nutrients, flow, light intensity, light spectrum, and time interval.

47. The method of claim 43, wherein method further comprises harvesting the aquatic biomass.

* * * * *